US010512752B2

(12) United States Patent
Tomes et al.

(10) Patent No.: US 10,512,752 B2
(45) Date of Patent: Dec. 24, 2019

(54) CATHETER TRAY, PACKAGING SYSTEM, AND ASSOCIATED METHODS

(71) Applicant: Medline Industries, Inc., Mundelein, IL (US)

(72) Inventors: Jennifer E. Tomes, Mundelein, IL (US); Deborah B. Adler, New York, NY (US); Kenneth S. Chua, Glenview, IL (US)

(73) Assignee: Medline Industries, Inc., Northfield, IL (US)

( * ) Notice: Subject to any disclaimer, the term of this patent is extended or adjusted under 35 U.S.C. 154(b) by 568 days.

(21) Appl. No.: 15/051,964

(22) Filed: Feb. 24, 2016

(65) Prior Publication Data

US 2016/0166800 A1   Jun. 16, 2016

Related U.S. Application Data

(63) Continuation of application No. 12/647,515, filed on Dec. 27, 2009, now abandoned, which is a (Continued)

(51) Int. Cl.
*A61M 25/00*   (2006.01)
*A61B 50/30*   (2016.01)
(Continued)

(52) U.S. Cl.
CPC .......... *A61M 25/002* (2013.01); *A61B 50/30* (2016.02); *A61B 50/33* (2016.02); *A61M 27/00* (2013.01);
(Continued)

(58) Field of Classification Search
CPC ................ A61M 25/002; A61M 27/00; A61M 2207/10; A61B 42/00; A61B 46/00;
(Continued)

(56) References Cited

U.S. PATENT DOCUMENTS 2,659,485 A   11/1953   Duley et al.
2,715,296 A   8/1955   Petit
(Continued)

FOREIGN PATENT DOCUMENTS

CN   201823147   5/2011
EP   2007/045943   4/2007
(Continued)

OTHER PUBLICATIONS

Chinese Application No. 201280035240.4; Filed May 24, 2012; Mailed Aug. 18, 2015.
(Continued)

*Primary Examiner* — Benjamin J Klein
(74) *Attorney, Agent, or Firm* — Philip H. Burrus, IV

(57) ABSTRACT

A tray (100) for accommodating a coiled medical device, such as a catheter assembly (700), includes a first compartment (101), a second compartment (102), and a third compartment (103). The catheter assembly (700) and devices associated with a catheterization procedure, such as syringes (701,702) containing sterile water and lubricating jelly and a specimen container (703) can be disposed within the tray. Printed instructions (1001) can be included with the tray (100). When a CSR wrap (1000) is disposed about the tray (100), the printed instructions can be placed atop the CSR wrap (1000) but beneath an outer sterile wrap (1002). The printed instructions (1001) can include a patient portion (1202) that is detachably coupled to a health care services portion (1201) such that it can be taken home with the patient after the procedure.

19 Claims, 17 Drawing Sheets

Related U.S. Application Data continuation-in-part of application No. 12/495,148, filed on Jun. 30, 2009, now Pat. No. 8,631,935.

(60) Provisional application No. 61/183,629, filed on Jun. 3, 2009.

(51) Int. Cl.
| | |
|---|---|
| *A61B 50/33* | (2016.01) |
| *A61M 27/00* | (2006.01) |
| *A61B 42/00* | (2016.01) |
| *A61B 46/00* | (2016.01) |
| *A61B 90/90* | (2016.01) |

(52) U.S. Cl.
CPC ............. *A61B 42/00* (2016.02); *A61B 46/00* (2016.02); *A61B 90/90* (2016.02); *A61B 2050/3008* (2016.02); *A61B 2050/3015* (2016.02); *A61M 2207/10* (2013.01)

(58) Field of Classification Search
CPC ......... A61B 50/30; A61B 50/33; A61B 90/90; A61B 2050/3015
See application file for complete search history.

(56) References Cited

U.S. PATENT DOCUMENTS

| | | | |
|---|---|---|---|
| 2,781,611 A | 2/1957 | West |
| 2,886,316 A | 5/1959 | Ayala |
| 2,947,415 A | 8/1960 | Garth |
| 2,954,642 A | 10/1960 | Roderick |
| 2,959,891 A | 11/1960 | Barnett et al. |
| 3,013,656 A | 12/1961 | Murphy, Jr. |
| 3,107,786 A | 10/1963 | Adelman |
| 3,133,635 A | 5/1964 | Morris |
| 3,166,189 A | 1/1965 | Disston |
| 3,315,802 A | 4/1967 | Maro |
| 3,329,261 A | 7/1967 | Serany, Jr. et al. |
| D209,641 S | 12/1967 | Goldberg |
| 3,379,339 A | 4/1968 | Asenbauer |
| 3,485,352 A | 12/1969 | Pilger |
| D218,077 S | 7/1970 | Gabriel |
| 3,542,019 A | 12/1970 | Gittins |
| 3,726,281 A | 4/1973 | Norton |
| 3,770,119 A | 11/1973 | Hultberg et al. |
| 3,851,649 A | 12/1974 | Villari |
| D234,404 S | 2/1975 | Merril |
| 3,901,235 A | 8/1975 | Patel et al. |
| D237,315 S | 10/1975 | Nowakowski |
| D237,317 S | 10/1975 | Nowkowski |
| 3,965,900 A | 6/1976 | Boedecker |
| 3,967,728 A | 7/1976 | Gordon et al. |
| 3,976,195 A | 8/1976 | Cohen |
| 3,978,983 A | 9/1976 | Brezetta |
| D242,654 S | 12/1976 | Rawls |
| 3,998,221 A | 12/1976 | Collins |
| D243,798 S | 3/1977 | Swartz |
| 4,011,944 A | 3/1977 | Cooley |
| 4,053,280 A | 10/1977 | Salisbury |
| 4,075,782 A | 2/1978 | Neuschatz |
| D248,871 S | 8/1978 | Forsman et al. |
| D249,362 S | 9/1978 | Forsman et al. |
| 4,140,127 A | 2/1979 | Ciani et al. |
| 4,160,505 A | 7/1979 | Rauschenberger |
| 4,170,300 A | 10/1979 | Pick |
| 4,226,328 A | 10/1980 | Beddow |
| 4,266,669 A | 5/1981 | Watson |
| 4,269,310 A | 5/1981 | Uson |
| 4,282,678 A | 8/1981 | Tsui |
| 4,307,539 A | 12/1981 | Klein |
| D262,995 S | 2/1982 | Gaba et al. |
| 4,334,537 A | 6/1982 | Peterson |
| D268,130 S | 3/1983 | Easton |
| 4,458,705 A | 7/1984 | Cawood |
| D275,886 S | 10/1984 | Sheward et al. |
| D276,462 S | 11/1984 | Villarreal |
| D277,508 S | 2/1985 | Clair |
| 4,501,363 A | 2/1985 | Isbey, Jr. |
| 4,523,679 A * | 6/1985 | Paikoff ............... A61L 2/04 206/363 |
| 4,530,349 A | 7/1985 | Metzger |
| D280,663 S | 9/1985 | Albon et al. |
| D280,933 S | 10/1985 | McLaughlin |
| D280,993 S | 10/1985 | Mariol |
| D283,051 S | 3/1986 | Fichera |
| D287,760 S | 1/1987 | Discko, Jr. |
| 4,761,008 A | 8/1988 | Huggins |
| 4,767,008 A | 8/1988 | Warnecke et al. |
| 4,795,441 A | 1/1989 | Bhatt |
| 4,811,847 A | 3/1989 | Reif |
| 4,828,113 A | 5/1989 | Friedland |
| 4,844,259 A | 7/1989 | Glowczewskie et al. |
| 4,858,821 A | 8/1989 | Bickelhaupt |
| D310,896 S | 9/1990 | Winjum |
| 4,991,877 A | 2/1991 | Lieberman |
| 5,007,535 A | 4/1991 | Meseke et al. |
| 5,024,326 A | 6/1991 | Sandel et al. |
| 5,031,768 A | 7/1991 | Fischer |
| 5,094,621 A | 3/1992 | Friedel |
| 5,163,557 A | 11/1992 | Sokolowski |
| 5,170,804 A | 12/1992 | Glassman |
| 5,197,885 A | 3/1993 | Friedel |
| D334,973 S | 4/1993 | Valentine et al. |
| D337,830 S | 7/1993 | Coyne et al. |
| 5,232,369 A | 8/1993 | Mavrikis |
| 5,242,398 A | 9/1993 | Knoll et al. |
| 5,244,394 A | 9/1993 | Serabian-Musto |
| D343,687 S | 1/1994 | Houghton et al. |
| 5,312,287 A | 5/1994 | Chuang |
| 5,314,339 A | 5/1994 | Aponte |
| 5,318,543 A | 6/1994 | Ross et al. |
| 5,324,201 A | 6/1994 | Friedel |
| 5,339,955 A | 8/1994 | Horan et al. |
| D351,661 S | 10/1994 | Fischer |
| 5,392,918 A | 2/1995 | Harrison |
| 5,411,437 A | 5/1995 | Weber et al. |
| 5,487,566 A | 1/1996 | Hedge, Jr. |
| D380,272 S | 6/1997 | Partika et al. |
| 5,665,945 A | 9/1997 | Oshima |
| D387,177 S | 12/1997 | Davis |
| D387,559 S | 12/1997 | Williamson |
| 5,713,778 A | 2/1998 | Rodeosevich et al. |
| 5,720,502 A | 2/1998 | Cain |
| 5,778,574 A | 7/1998 | Reuben |
| 5,779,053 A | 7/1998 | Partika |
| 5,795,213 A | 8/1998 | Goodwin |
| 5,810,738 A | 9/1998 | Thomas, II |
| 5,820,441 A | 10/1998 | Pracas |
| 5,827,262 A | 10/1998 | Neftel et al. |
| 5,829,790 A | 11/1998 | Phillips |
| 5,872,262 A | 2/1999 | Dolle, III et al. |
| 5,931,303 A | 8/1999 | Salvadori |
| 5,941,241 A | 8/1999 | Weinstein et al. |
| 5,947,284 A | 9/1999 | Foster |
| 5,954,369 A | 9/1999 | Seabrook |
| 5,975,295 A | 11/1999 | Diamond |
| 6,004,136 A | 12/1999 | Ehrenpreis |
| 6,012,586 A | 1/2000 | Misra |
| 6,068,121 A | 5/2000 | McGlinch |
| 6,089,943 A | 7/2000 | Lo |
| 6,142,152 A * | 11/2000 | Gawarecki ............ A61B 50/13 128/849 |
| 6,158,437 A | 12/2000 | Vagley |
| 6,159,017 A | 12/2000 | Coomansingh |
| D442,697 S | 5/2001 | Hajianpour |
| D450,130 S | 11/2001 | Goldstein |
| D450,391 S | 11/2001 | Hunt et al. |
| 6,330,427 B1 | 12/2001 | Tabachnik |
| 6,361,396 B1 | 3/2002 | Snyder et al. |
| 6,382,212 B1 | 5/2002 | Borchard |
| 6,405,863 B1 | 6/2002 | Dhindsa |
| 6,454,097 B1 | 9/2002 | Blanco |
| 6,579,271 B1 | 6/2003 | Aruffo et al. |

(56) References Cited

U.S. PATENT DOCUMENTS

| | | |
|---|---|---|
| 6,659,506 B1 | 12/2003 | Erisalu |
| 6,681,933 B1 | 1/2004 | Demsien et al. |
| 6,769,546 B2 | 8/2004 | Busch |
| D495,491 S | 9/2004 | Ramirez |
| 6,793,078 B2 | 9/2004 | Roshdy |
| 6,840,379 B2 | 1/2005 | Franks-Farah et al. |
| 6,896,141 B2 | 5/2005 | McMichael et al. |
| 6,915,901 B2 | 7/2005 | Feinberg |
| 6,926,708 B1 | 8/2005 | Franks-Farah et al. |
| 6,948,742 B2 | 9/2005 | Buck |
| 7,048,120 B2 | 5/2006 | Pond |
| 7,066,328 B2 | 6/2006 | Pulsifer |
| D530,920 S | 10/2006 | Snell |
| D547,064 S | 7/2007 | Snell |
| D549,454 S | 8/2007 | Åhman |
| 7,264,869 B2 | 9/2007 | Tobita |
| 7,278,987 B2 | 10/2007 | Solazzo |
| D557,047 S | 12/2007 | Dretzka |
| D561,473 S | 2/2008 | Phillips et al. |
| D563,673 S | 3/2008 | Dretzka |
| 7,401,703 B2 | 7/2008 | McMichael |
| 7,434,687 B2 | 10/2008 | Itou et al. |
| D579,662 S | 11/2008 | Dretzka |
| D590,596 S | 4/2009 | Dretzka |
| D596,311 S | 7/2009 | Antons |
| 7,624,869 B2 | 12/2009 | Primer |
| D609,819 S | 2/2010 | Tomes et al. |
| D612,153 S | 3/2010 | Liao |
| 7,785,312 B2 | 8/2010 | Thorne |
| 7,789,873 B2 | 9/2010 | Kubalak |
| D636,894 S | 4/2011 | Tomes et al. |
| D638,137 S | 5/2011 | Gross et al. |
| D662,218 S | 6/2012 | Pittman |
| 8,448,786 B2 | 5/2013 | Tomes et al. |
| D688,461 S | 8/2013 | Ambrefe et al. |
| 8,628,549 B2 | 1/2014 | To et al. |
| 8,631,935 B2 | 1/2014 | Tomes et al. |
| 8,678,190 B2 | 3/2014 | Tomes et al. |
| 8,708,999 B2 | 4/2014 | Hong et al. |
| D708,347 S | 7/2014 | Lober |
| D708,759 S | 7/2014 | Heyman et al. |
| D720,470 S | 12/2014 | Lober |
| D720,471 S | 12/2014 | Angel et al. |
| 9,084,593 B2 | 7/2015 | Yakel et al. |
| D742,028 S | 10/2015 | Hutchison |
| 9,283,352 B2 | 3/2016 | Tomes et al. |
| 9,522,753 B2 | 12/2016 | Tomes et al. |
| D779,082 S | 2/2017 | Andre et al. |
| D800,337 S | 10/2017 | Daines |
| 9,795,761 B2 | 10/2017 | Lockwood et al. |
| 9,808,400 B2 | 11/2017 | Tomes et al. |
| 10,251,812 B2 | 4/2019 | Tomes et al. |
| 2002/0185406 A1 | 12/2002 | Massengale |
| 2003/0031995 A1 | 2/2003 | Laura |
| 2003/0038475 A1 | 2/2003 | Stancil |
| 2003/0075474 A1 | 4/2003 | Moyer et al. |
| 2003/0159966 A1 | 8/2003 | McMichael et al. |
| 2003/0159969 A1 | 8/2003 | McMichael et al. |
| 2004/0004019 A1 | 1/2004 | Busch |
| 2004/0055919 A1 | 3/2004 | Rowe et al. |
| 2004/0161732 A1 | 8/2004 | Stump |
| 2004/0180822 A1 | 9/2004 | Grafton |
| 2004/0195145 A1 | 10/2004 | Roshdy |
| 2004/0238391 A1 | 12/2004 | Pond |
| 2005/0022822 A1 | 2/2005 | Santilli |
| 2005/0101905 A1 | 5/2005 | Merry |
| 2005/0228691 A1 | 10/2005 | Paparo |
| 2005/0256453 A1 | 11/2005 | Nagamatsu |
| 2005/0285385 A1 | 12/2005 | Bova |
| 2006/0009742 A1 | 1/2006 | Solazzo |
| 2006/0011501 A1 | 1/2006 | Itou |
| 2006/0029912 A1 | 2/2006 | Kearby et al. |
| 2006/0088355 A1 | 4/2006 | Ribi |
| 2006/0096877 A1 | 5/2006 | Khajavi et al. |
| 2006/0186010 A1 | 8/2006 | Warnack |
| 2006/0264822 A1 | 11/2006 | Nagamatsu |
| 2006/0271019 A1 | 11/2006 | Stoller |
| 2007/0026472 A1 | 2/2007 | Prokash et al. |
| 2007/0060908 A1 | 3/2007 | Webster et al. |
| 2007/0065792 A1 | 3/2007 | Schubarth |
| 2007/0084742 A1 | 4/2007 | Miller et al. |
| 2007/0088330 A1 | 4/2007 | House |
| 2007/0095699 A1 | 5/2007 | Frieze |
| 2007/0142786 A1 | 6/2007 | Lampropoulos |
| 2007/0161971 A1 | 7/2007 | House |
| 2007/0203464 A1 | 8/2007 | Green et al. |
| 2007/0225687 A1* | 9/2007 | House ............... A61M 25/0017 604/544 |
| 2007/0299431 A1 | 12/2007 | Jakubowski et al. |
| 2008/0116106 A1 | 5/2008 | Lampropoulos et al. |
| 2008/0121553 A1 | 5/2008 | Gobel |
| 2008/0221515 A1 | 9/2008 | Nagamatsu |
| 2008/0249476 A1 | 10/2008 | Bierman et al. |
| 2008/0283426 A1* | 11/2008 | Primer ............... A61F 13/8405 206/232 |
| 2008/0283433 A1 | 11/2008 | Primer |
| 2009/0004055 A1 | 1/2009 | Darrigrand et al. |
| 2009/0071854 A1 | 3/2009 | Martin |
| 2009/0152160 A1 | 6/2009 | Thompson et al. |
| 2009/0184026 A1 | 7/2009 | Massengale et al. |
| 2009/0194453 A1 | 8/2009 | Thorne et al. |
| 2009/0234346 A1 | 9/2009 | McBride et al. |
| 2009/0236259 A1 | 9/2009 | Hicks |
| 2009/0318783 A1* | 12/2009 | Rohde ............... A61B 5/073 600/302 |
| 2010/0274205 A1* | 10/2010 | Morelli ............... A61M 1/0088 604/290 |
| 2010/0307942 A1 | 12/2010 | Tomes et al. |
| 2010/0311026 A1 | 12/2010 | Tomes et al. |
| 2011/0107494 A1 | 5/2011 | Haines |
| 2011/0155599 A1 | 6/2011 | Yakel et al. |
| 2011/0232234 A1 | 9/2011 | Lockwood et al. |
| 2011/0284410 A1 | 11/2011 | Lockwood |
| 2011/0297147 A1 | 12/2011 | Lick et al. |
| 2012/0145589 A1 | 6/2012 | Macinnes et al. |
| 2014/0110296 A1 | 4/2014 | Terzibashian |

FOREIGN PATENT DOCUMENTS

| | | |
|---|---|---|
| JP | 2007-229520 | 9/2007 |
| WO | 2005/027767 | 3/2005 |
| WO | 2006/114466 | 11/2006 |
| WO | 2007/045943 | 4/2007 |

OTHER PUBLICATIONS

Dictionary definition m-w. URL:<http://ww.merriam-webster.com/dictionary/reassure>. Retrieved from Internet Dec. 10, 2013.

Dictionary definition m-w. URL:<http://www.merriam-webster.com/dictionary/brave>. Retrieved fro Internet Dec. 10, 2013.

Dover Intermittent Catheter Tray—14 fr, Red Rubber; Website http://tinyurl.com/o4esrwh; Unknown Publication Date.

Lion King Sticker website. URL: <http://tlkobession.wuffpaws.org/OldSite/games/games2.html>. 1996 Retrieved from Internet Dec. 10, 2013.

Lion Sticker Activity Book website. URL: <http://www.amazon.com/Disneys-Simbas-Pride-Sticker-Activity/dp/B0018DOJZA>. 1998 Retrieved from Internet Dec. 10, 2013.

*Medline Industries Inc.* vs *C.R. Bard, Inc.*; C R. Bard's Final LPR 2.3 Contentions; Civil Action No. 1:17-cv-7216; Judge Sara L. Ellis; Filed Jul. 24, 2018.

*Medline Industries Inc.* vs *C.R. Bard, Inc.*; Exhibit A—C. R. Bard's Final LPR 2.3 Contentions; Civil Action No. 1:17-cv-7216; Judge Sara L. Ellis; Filed Jul. 24, 2018.

*Medline Industries Inc.* vs *C.R. Bard, Inc.*; Exhibit B—C. R. Bard's Final LPR 2.3 Contentions; Civil Action No. 1:17-cv-7216; Judge Sara L. Ellis; Filed Jul. 24, 2018.

*Medline Industries Inc.* vs *C.R. Bard, Inc.*; Exhibit C—C. R. Bard's Final LPR 2.3 Contentions; Civil Action No. 1:17-cv-7216; Judge Sara L. Ellis; Filed Jul. 24, 2018.

(56) References Cited

OTHER PUBLICATIONS

*Medline Industries Inc.* vs *C.R. Bard, Inc.*; Exhibit C to Declaration of Nicole M. Smith; Civil Action No. 1:14-cv-03618; Judge John 2. Lee; Filed Jun. 4, 2016.
*Medline Industries Inc.* vs *C.R. Bard, Inc.*; Exhibit D—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit E—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit F—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit G—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit H—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit I—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit J—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit K—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit L—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit M—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit N—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit O—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit P—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit Q—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit R—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit S—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit T—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; C.R. Bard's LPR 3.1 Contentions; Civil Action No. 1:16-cs-3529; Judge Sharon Johnson Coleman; Filed Aug. 26, 2016.
*Medline Industries Inc.* vs *C.R. Bard, Inc.*; Exhibit B to C R. Bard's LPR 2.3 Contentions; Civil Action No. 1:17-cv-7216; Judge Sara L. Ellis; Filed Jan. 16, 2018.
*Medline Industries* vs. *CR Bard, Inc.*; No. 14-cv-3618; C.R. Bard's LPR 3.1 Contentions; Filed Nov. 24, 2015.
*Medline Industries, Inc.* vs *C.R. Bard, Inc.*; No. 1:14-cv-03618; Medline Industries Inc's Opposition to C.R.Bard Inc's Motion for Leave to File Second Amended Answer to Add Counterclaim; Filed Oct. 20, 2015.
*Medline Industries, Inc.* vs *C.R. Bard, Inc.*; No. 1:14-cv-03618; Medline Industries, Inc.'s Response to C.R. Bard's Initial Invalidity Contentions; Exhibits A-H; Dated Sep. 19, 2014.
*Medline Industries, Inc.* vs *C.R. Bard, Inc.*; No. 1:14-cv-03618; Notice of Medline Industries Inc's Motion to Dismiss C.R. Bard Inc's Inequitable Conduct Counterclaim and to strike affirmative defense for the '786 Patent; Filed Oct. 20, 2015.
*Medline Industries, Inc.* vs *C.R. Bard, Inc.*; No. 1:14-cv-03618; Response to Medline Industries, Inc.'s First Set of Interrogatories; Dated Sep. 26, 2014.
*Medline Industries, Inc.* vs *C.R. Bard, Inc.*; No. 1:14-cv-03618; Responses to Medline Industries, Inc.'s First set of Requests for the Production of Documents; Dated Sep. 26, 2014.
*Medline Industries, Inc.* vs *C.R. Bard, Inc.*; No. 14-cv-3618; C.R. Bard's LPR 2.3 Contentions—Initial Non-Infringement; Exhibits 1 and A-H; Dated Sep. 5, 2014.
*Medline Industries, Inc.* vs *C.R. Bard, Inc*: Transcript of Proceedings—Claim Construction Hearing: Civil Action No. 1:14-cv-3618. Judge John Z. Lee; Dated Jan. 11, 2017.
Naming Characters on Cards website. URL:<https://web.archive.org/web/20060219171403/http://www.hubbardscupboard.org/brown_bear_brown_bear.html>. (2006) . . . Retrieved form Internet Dec. 11, 2013.
Notice of Allowance; EP Application No. 10251025.2-1501; Reference P112645EP00; dated Feb. 18, 2016.
*Medline Industries Inc.* vs *C.R Bard, Inc.*, Bard Opening Claim Construction Brief; Civil Action No. 1:16-cv-03529; Judge Sharon Johnson Coleman; Filed Nov. 17, 2017.
"Article 94(3) EPC Examination", European Application No. 10 251 025.2-1501; Reference P112645EP00; dated Mar. 13, 2015.
"Australian First Exam Report", AU Patent Application No. 2011351971; Patent Examination Report No. 1; dated Jul. 25, 2015.
"Bard IPR Exhibit", "Inter Partes Review Petition", IPR Exhibit—Carrow Declaration for U.S. Pat. No. 8,631,935; Susan Carrow Declaration; Mailed Dec. 30, 2014.
"Bard Medical Division Care & Catheterization Script", Care & Catheterization/Preventing UTI Script for education video; Preventing UTI: Care and Catheterization Techniques; Copyright 2006; AV0512-06 R12/05 XXX.
"Bard Publication", "A few important words about Catheter Care"; C.R. Bard, Inc.; Copyright 2001 C.R. Bard, Inc.
"Bardex I.C. Complete Care StateLock Device 350 ml Urine Meter Foley Tray with Bacteriostatic Collection System", Bard Infection Control System; Bardex I.C. Complete Care Directions for Use; Copyright Dated Sep. 2006.
"Bardex I.C. Infection Control 350ml Urine Meter Foley Tray", Bard Infection Control System; Bardex I.C. Urine Meter Foley Tray Directions for Use; Copyright Dated 2006.
"Bardex I.C. Infection Control Foley Tray", Bard Infection Control System; Bardex I.C. Directions for Use Infection Control Foley Tray; Copyright Dated 2006.
"EPO Intent to Grant", EPO Application No. 10251024.5; Filed Jun. 2, 2010; dated Nov. 2, 2012.
"Examiner's Answer", U.S. Appl. No. 13/153,265, filed Jun. 3, 2011; dated Dec. 17, 2013.
"Extended EPO Exam Report", EPO App No. 10251025.2; Filed Jun. 2, 2010; dated Dec. 17, 2013.
"Instructions", Naming a character website. URL: <https://web.archive.org/web/20080410122058/http://www.wilihow.com/Make-Your-Own-Anime-or-Mange-Character>. 2008.Retreived from Internet Dec. 10, 2013.
"Intent to Grant", Chinese Application No. 201180066491.4; Filled Dec. 30, 2011; dated Jul. 6, 2016.
"Intent to Grant", European Application No. 16177903.8-1501; Reference No. SJG/P112645EP02; dated Sep. 18, 2017.
"Inter Partes Review—Patent Owner Response", Inter Partes Review—Patent Owner Response; U.S. Pat. No. 8,631,935; Inter Partes Review No. IPR2015-00513; Filed Apr. 21, 2015.
"Inter Partes Review—Patent Owner Response", Inter Partes Review—Patent Owner Response; U.S. Pat. No. 8,448,786; IPR2015-00509; Filed Apr. 22, 2015.
"Inter Partes Review—Patent Owner Response", Inter Partes Review—Patent Owner Response; U.S. Pat. No. 8,631,935; Inter Partes Review No. IPR2015-00511; Filed Apr. 22, 2015.

(56) References Cited

OTHER PUBLICATIONS

"Inter Partes Review—Patent Owner Response", Inter Partes Review—Patent Owner Response; U.S. Pat. No. 8,678,190; Inter Partes Review No. IPR2015-00514; Filed Apr. 21, 2015.
"Inter Partes Review Petition", Exhibit—Amendment filed on Apr. 3, 2013 for U.S. Appl. No. 12/495,148, filed Jun. 30, 2009.
"Inter Partes Review Petition", Exhibit—Bard DFU; Bardex Infection Control Foley Tray; Copyright 2006, publication date unknown.
"Inter Partes Review Petition", Exhibit—Bardex DFU; Directions for Use/Patient Education Information—Urology; Unknown Publication Date.
"Inter Partes Review Petition", Exhibit—Declaration of Susan Carrow for U.S. Pat. No. 8,631,935 claims 1-4 and 11-20; Mailed Dec. 30, 2014.
"Inter Partes Review Petition", Exhibit—Dorland's Definition of Bag; Dorland's Illustrated Medical Dictionary; 31st Edition; Publication Date Unknown.
"Inter Partes Review Petition", Exhibit—EC Guideline 1998; "A Guideline on the Readability of the Label and Package Leaflet of Medicinal Products for Human Use"; Published Sep. 29, 1998 (Sep. 29, 1998); Mailed Dec. 30, 2014.
"Inter Partes Review Petition", Exhibit—Encyclopedia Dictionary of Medicine, Nursing and Allied Health; Miller Keane, Seventh Edition.
"Inter Partes Review Petition", Exhibit—FAQs "Catheter-Associated Urinary Tract Infection"; Unknown Publisher; Unknown Publication Date.
"Inter Partes Review Petition", Exhibit —FDA Article; Guidance for the Content of Premarkt Notifications fro Conventional and Antimicrobial Foley Catheters; http://www.fda.gov/medicaldevices/deviceregulationandguidance/guidancedocuments/ucm080884.htm; Unknown Publication Date.
"Inter Partes Review Petition", Exhibit—Health Protection Scotland; CAUTI Maintenance Bundel; Version 2, Feb. 2008.
"Inter Partes Review Petition", Exhibit—Infection Control Today Article; Medical Center Cuts Catheterizations by 21 Percent with Foley Catheter Management System; Published 2010.
"Inter Partes Review Petition", Exhibit—Kimmel Declaration for U.S. Pat. No. 8,631,935 claims 1-4 and 11-20; Declaration of Dr. Robert M. Kimmel; Mailed Dec. 30, 2014.
"Inter Partes Review Petition", Exhibit—Medical News Today Article; 'Getting to Zero:' Medlines' Erase Cauti Program Helps Hospitals Reduce Catheter Use by 20 Percent; Article Date Apr. 13, 2011.
"Inter Partes Review Petition", Exhibit—Medline Initial Infringement Contentions; *Medline Industries* vs. *C.R. Bard*; Dated Aug. 22, 2014.
"Inter Partes Review Petition", Exhibit —Morning Start Article; "Floyd Medical Center Reduces Catheter-Associated Urinary Tract Infections 83 Percent and Catheter Use by 23 Percent"; Published Jan. 2011.
"Inter Partes Review Petition", Exhibit —Mosby's Pocket Guide Excerpt; Mosby's Pocket Guide to Basic Skills and Procedures; Sixth Edition; Perry & Potter; "Urinary Catheter: Indwelling, Straight, Care and Removal"; Unknown Publication Date.
"Inter Partes Review Petition", Exhibit—Nursing Standard; Article in Learning Zone—Continue Professional Development; "Reducing the risks associated with urinary catheters"; Published Mar. 25, 2009.
"Inter Partes Review Petition", Exhibit—RCE Filed Nov. May 31, 2011 for U.S. Appl. No. 12/495,148, filed Jun. 30, 2009.
"Inter Partes Review Petition", Exhibit—Response to Office Action in U.S. Appl. No. 12/495,148, filed Jun. 30, 2009; Response Filed Nov. 19, 2010.
"Inter Partes Review Petition", Exhibit—Soroka Glossary 'Bag'; Illustrated Glossary of Packaging Terminology, second edition; Walter Soroka; publication unknown.
"Inter Partes Review Petition", Exhibit —Soroka Glossary_wrap; Illustrated Glossary of Packaging Terminology; second edition; publication date unknown.
"Inter Partes Review Petition", Exhibit—The Journal of Healthcare Contracting, Oct. 2012; "Catheter-associated urinary tract infections".
"Inter Partes Review Petition", Exhibit—Websters Dictionary Definition of Dispose; Webster's Third New International Dictionary; Copyright 2003; publication date unknown.
"Inter Partes Review Petition", Exhibit; Carrow CV—Susan Carrow CV; Mailed Dec. 30, 2014.
"Inter Partes Review Petition", Exhibit; EC Guideline 2009; "Guideline on the Readability of the Labelling and Package Leaflet of Medicinal Products for Human Use"; Revision 1 Published Jan. 12, 2009 (Jan. 12, 2009); Mailed Dec. 30, 2014.
"Inter Partes Review Petition", Exhibit; Kimmel CV—Dr. Robert M. Kimmel; Mailed Dec. 30, 2014.
"Inter Partes Review Petition", IPR Exhibit—Carrow Declaration for U.S. Pat. No. 8,631,935 claims 1-4 and 11-20; Susan Carrow Declaration; Mailed Dec. 30, 2014.
"Inter Partes Review Petition", IPR Exhibit—Carrow Declaration for U.S. Pat. No. 8,768,190; Declaration of Susan Carrow; Mailed Dec. 30, 2014.
"Inter Partes Review Petition", IPR Exhibit—Kimmel Declaration U.S. Pat. No. 8,448,786; Dr. Robert M. Kimmel Declaration; Received Dec. 30, 2014.
"Inter Partes Review Petition", IPR Exhibit—Kimmel Declaration for U.S. Pat. No. 8,631,935 claims 1-4 and 11-20; Declaration of Dr. Robert M. Kimmel; Mailed Dec. 30, 2014.
"Inter Partes Review Petition", IPR Exhibit—Kimmel Declaration for U.S. Pat. No. 8,631,935 claims 7-8, 10, 21-23, 25, 27-28, and 30-34; Declaration of Dr. Robert M. Kimmel; Mailed Dec. 30, 2014.
"Inter Partes Review Petition", IPR Exhibit—Kimmel Declaration for U.S. Pat. No. 8,768,190; Declaration of Dr. Robert M. Kimmel; Mailed Dec. 30, 2014.
"Inter Partes Review Petition", IPR Exhibit—Susan Carrow Declaration U.S. Pat. No. 8,448,786; mailed Dec. 30, 2014.
"Inter Partes Review Petition for U.S. Pat. No. 8,448,786", U.S. Pat. No. 8,448,786; Filed Dec. 30, 2014; Mailed Dec. 30, 2014.
"Inter Partes Review Petition for U.S. Pat. No. 8,631,935", Inter Partes Review Petition for U.S. Pat. No. 8,631,935 for claims 1-4 and 11-20; Filed Dec. 30, 2014.
"Inter Partes Review Petition for U.S. Pat. No. 8,631,935", Inter Partes Review Petition for U.S. Pat. No. 8,631,935 for Claims 7-8, 10, 21-23, 25, 27-28, and 30-34; Filed Dec. 30, 2014.
"Inter Partes Review Petition for U.S. Pat. No. 8,678,190", Inter Partes Review Petition for U.S. Pat. No. 8,678,190; Filed Dec. 30, 2014.
"Inter Partes Review Petition for U.S. Pat. No. 9,745,088", IPR-0036; Filed Oct. 4, 2018.
"Inter Partes Review Petition for U.S. Pat. No. 9,745,088", IPR2019-0035, filed Oct. 4, 2018.
"IPR 2015-00514—Patent Owner's Objection to Evidence", IPR 201500514—Patent Owner's Objection to Evidence Submitted During a Preliminary Proceeding; U.S. Pat. No. 8,678,190; Mailed Jul. 13, 2015.
"IPR 2015-00514—Patent Owner's Request for Adverse Judgment", U.S. Pat. No. 8,678,190; Mailed Jul. 23, 2015.
"IPR 2015-00514—Request for Rehearing Denied", IPR2015-00514; U.S. Pat. No. 8,678,190; Decision on Request for Rehearing—Denied; Mailed Jul. 16, 2015.
"IPR 2015-00514 Petitioner's Request for Rehearing", IPR 2015-00514 Petitioner's Request for Rehearing; U.S. Pat. No. 8,678,190; Dated Jul. 10, 2015.
"IPR Exhibit 1002", Declaration of Pliska; IPR2019-0035, Filed Oct. 4, 2018.
"IPR Exhibit 1003", Declaration of Yun; IPR2019-0035; Filed Oct. 4, 2018.
"IPR Petition Exhibit 1016", Excerpt from "The Design of Everyday Things"; IPR2019-0035; Filed Oct. 4, 2018.
"IPR0215-00513 Scheduling Order", U.S. Pat. No. 8,631,935; Mailed Jul. 15, 2015.
"IPR2015-00509 Institution Decision", IPR2015-00509; U.S. Pat. No. 8,448,786; Mailed Jul. 15, 2015; Decision Denying Institution of Inter Partes Review.

(56) References Cited

OTHER PUBLICATIONS

"IPR2015-00511 Institution Decision", IPR2015-00511; U.S. Pat. No. 8,631,935; Entered Jul. 15, 2015; Decision Denying Institution of Inter Partes Review.
"IPR2015-00513—Request for Adverse Judgement", IPR2015-00513—Request for Adverse Judgement; Granted—Proceedings Terminated; U.S. Pat. No. 8,631,935; Entered Aug. 11, 2015.
"IPR2015-00513—Patent Owner's Request for Adverse Judgement", U.S. Pat. No. 8,631,935; Mailed Jul. 23, 2015.
"IPR2015-00513 Institution Decision", IPR2015-00513 Institution Decision; U.S. Pat. No. 8,631,935; Entered Jul. 15, 2015; Decision Institution of Inter Partes Review.
"IPR2015-00514—Scheduling Order", U.S. Pat. No. 8,678,190; Mailed Jun. 26, 2015.
"IPR2015-00514 Decision Institution of Inter Partes Review", IPR2015-00514; U.S. Pat. No. 8,678,190; Mailed Jun. 26, 2015; Decision Institution of Inter Partes Review.
"IPR2015-00514 Judgement—Termination of Proceeding", U.S. Pat. No. 8,678,190; Mailed Jul. 24, 2015.
"Medline Catalog", Argyle Trocar Catheter Kits by Covidien; http://www.medline.com/sku/item/MDPSWD565028; Unknown Publication Date but believed to be prior to filing of present application.
"Medline Catalog", Argyle Turkel Safety Thoracentesis System by Covidien; 6; http://www.medline.com/sku/item/MDPKDL5016; Unknown Publication Date but believed to be prior to filing of present application.
"Medline Catalog", Argyle Turkel Safety Thoracentesis System by Covidien; http://www.medline.com/sku/item/MDPKDL5014; Unknown Publication Date but believe to be prior to filing of present application.
"Medline Catalog", Paracentesis Trays by Covidien; http://www.medline.com/sku/item/MDPSWD568006; Unknown Publication Date but believed to be prior to filing of present application.
"Medline Catalog", Paracentesis Trays by Halyard Health; http://www.medline.com/sku/item/MDPBAA61450; Unknown Publication Date but believed to be prior to filing of present application.
"Medline Catalog", Safe-T Thoracentesis/Paracentesis Tray by Carefusion; http://www.medline.com/sku/item/MDPBXTTPT1000SP; Unknown publication date but believed to be prior to filing of present application.
"Medline Catalog", Thoracentesis Trays by Carefusion; http://www.medline.com/sku/item/MDPBXTPIG1280K; Unknown publication date but believed to be prior to filing of present application.
"Medline Catalog", Turkel Safety Thoracentesis Procedure Trays by Covidien; 5; http://www.medline.com/sku/item/MDPKDL566075; Unknown Publication date but believed to be prior to present application filing date.
"Medline Catalog", Turkel Safety Thoracentesis Procedure Trays by Covidien; http://www.medline.com/jump/sku/x/MDPKDL566059; Unknown Publication date but believed to be prior to present application filing date.
"NonFinal Office Action", U.S. Appl. No. 13/680,902, filed Apr. 11, 2014; dated Dec. 2, 2014.
"Notice of Acceptance", Australian Application No. 2011351971; Filed Dec. 30, 2011; dated May 13, 2016.
"Notice of Allowance", Canadian Application No. 2,705,647; Filed May 27, 2010; dated Oct. 12, 2017.
"Notice of Allowance", Candaian Application No. 2,705,670; dated Nov. 3, 2017.
"Notice of Allowance", Chinese Application No. 201280035240.4; dated Nov. 7, 2017.
"Office Action", Australian Application No. 2011351971; dated Feb. 18, 2016.
"Office Action", Chinese Application No. 201180066491.4; dated Mar. 24, 2015.
"Office Action", Chinese Application No. 201180066491.4; dated Nov. 11, 2015.
"Office Action", Chinese Application No. 201280035246.1; Filed May 11, 2012; dated Jul. 15, 2016.
"Office Action", Chinese Application No. 201280035246.1; Filed May 11, 2012; dated Nov. 28, 2016.
"Office Action Received", Chinese App No. 201280035246.1; NonFinal OA; dated Sep. 16, 2015.
"Publication", European Commission: Pharmaceutical Committee "A Guideline on the Readability of the Label and Package Leaflet of Medicinal Products for Human Use"; Dated Sep. 29, 1998.
"Second Office Action", Chinese Application No. 201280035240.4; dated Jun. 23, 2016.
"Third Office Action", Chinese Application No. 201280035240.4; dated Apr. 1, 2017.
"YouTube Training Video", https://www.youtube.com/watch?v=YwqcRUP35nl&list=UUG7a6tFPh1wvF0QDMZ3Dar; Unknown Publication Date but believed to be prior to filing of present application.
"YouTube Training Video", https://www.youtube.com/watch?v=ISBya_5clM; Unknown Publication Date but believed to be prior to filing of present application.
Byun, Sung C., "PCT Search Report", PCT/US2011/068193; Filed Dec. 30, 2011; dated Aug. 22, 2012.
Byun, Sung C., "PCT Search Report", PCT/US2012/039311; Filed May 24, 2011; dated Oct. 25, 2012.
Byun, Sung Cheal, "PCT Search Report and Written Opinion", PCT/US2012/037524; Filed May 11, 2012; dated Nov. 16, 2012.
Cavanna, Mark, "Ex Parte Quayle Action", U.S. Appl. No. 29/380,474, filed Dec. 6, 2010; Mailed Aug. 14, 2012.
Cavanna, Mark, "Final OA", U.S. Appl. No. 29/479,600, filed Jan. 17, 2014; Mailed Jun. 1, 2017.
Cavanna, Mark, "NonFinal OA", U.S. Appl. No. 29/479,600, filed Jan. 17, 2014; Mailed Jan. 3, 2018.
Cavanna, Mark, "NonFinal Office Action", U.S. Appl. No. 29/380,474, filed Dec. 26, 2012; dated Mar. 27, 2012.
Cavanna, Mark, "Non-Final Office Action", U.S. Appl. No. 29/479,600, filed Jan. 17, 2014; dated Sep. 26, 2016.
Cavanna, Mark, "Notice of Allowance", U.S. Appl. No. 29/338,022, filed Jun. 3, 2009; dated Oct. 1, 2009.
Cavanna, Mark, "Notice of Allowance", U.S. Appl. No. 29/362,279, filed May 21, 2010, dated Sep. 19, 2011.
Cavanna, Mark, "Notice of Allowance", U.S. Appl. No. 29/444,526, filed Jan. 31, 2013; dated Oct. 17, 2013.
European Patent Office, "Extended EPO Search Report", Application No. 10251024.5, In the Name of Medline Industries, dated Oct. 18, 2010.
European Patent Office, "Extended EPO Search Report", EPO Application No. 10251025.2, In the Name of Medline Industries, dated Sep. 29, 2010.
Examiner, Chinese Patent Office "First Office Action", CN Application No. 201020219785.9; dated Nov. 18, 2010; Filed June 3, 2010.
Gilligan, C. Luke "Notice of Allowance", U.S. Appl. No. 13/153,265, filed Jun. 3, 2011; dated Jun. 15, 2017.
Gimenez Burgos, R , "European Examination Report", European Application No. 11 854 003.8-1659; Ref SJG/P128064EP00; dated Jan. 22, 2015.
Gimenez Burgos, R , "Extended European Search Report", 11854003.8; Filed Dec. 30, 2011; dated Jun. 3, 2014.
Gimenez Burgos, R , "Extended European Search Report", EPO App No. 12 79 3939; Reference No. SJG/P130269EP00; dated Jan. 27, 2015.
Gimenez Burgos, R , "Extended European Search Report", EU App No. 12792423.1-1659/2713933; PCT/US2012039311; REference No. SJG/P130270EP00; dated Jan. 27, 2015.
Hand, Melanie J., "Final OA", U.S. Appl. No. 12/785,064, filed May 21, 2010; Mailed Jun. 5, 2013.
Hand, Melanie J., "NonFinal OA", U.S. Appl. No. 12/785,064, filed May 21, 2010; Mailed Feb. 1, 2013.
Hand, Melanie J., "NonFinal OA", U.S. Appl. No. 13/115,053, filed Jun. 7, 2011; Mailed May 9, 2013.
Hand, Melanie J., "NonFinal OA", U.S. Appl. No. 13/155,026, filed Jun. 7, 2011; Mailed Nov. 30, 2012.
Hand, Melanie J., "NonFinal OA", U.S. Appl. No. 13/860,902, filed Apr. 11, 2013; Mailed Apr. 1, 2016.
Hand, Melanie J., "NonFinal OA", U.S. Appl. No. 14/165,044, filed Jan. 27, 2014; Mailed Oct. 26, 2015.

(56) References Cited

OTHER PUBLICATIONS

Hand, Melanie J., "Notice of Allowance", U.S. Appl. No. 13/155,026, filed Jun. 7, 2011; dated Feb. 1, 2013.
Hand, Melanie J., "Notice of Allowance", U.S. Appl. No. 13/155,054, filed Jun. 7, 2011; dated Oct. 28, 2013.
Hand, Melanie J., "Notice of Allowance", U.S. Appl. No. 13/860,902, filed Apr. 11, 2013; dated Aug. 4, 2015.
Hand, Melanie JO, "Appeal Decision", U.S. Appl. No. 12/785,064, filed May 21, 2010; Mailed May 18, 2016.
Hand, Melanie JO, "Final OA", U.S. Appl. No. 13/860,902, filed Apr. 11, 2013; Mailed May 22, 2015.
Long, Fonya M, "Appeal Decision", U.S. Appl. No. 13/154,265, filed Jun. 3, 2011; Mailed Oct. 6, 2016.
MacKenzie, Kristian, "Office Action", Canadian Application No. 2,705,647; Ref No. 15486-P37235CA00 10055U CA; dated Feb. 10, 2017.
MacKenzie, Kristian, "Office Action", Canadian Application No. 2,705,647; Ref No. 15468-P37235CA00; dated Apr. 21, 2016.
MacKenzie, Kristian, "Office Action", Canadian Application No. 2,705,670; Attorney Ref No. 15468-P37238CA00; dated Feb. 10, 2017.
MacKenzie, Kristian, "Office Action", Canadian Application No. 2,705,670; Ref No. 15468-8; dated Apr. 25, 2016.
Marcetich, Adam, "Notice of Allowance", U.S. Appl. No. 13/860,902, filed Apr. 11, 2013; dated Nov. 8, 2016.
Marcetich, Adam, "Notice of Allowance", U.S. Appl. No. 13/860,902, filed Apr. 11, 2013; dated Sep. 14, 2016.
Marcetich, Adam, "Notice of Allowance", U.S. Appl. No. 14/165,044, filed Jan. 27, 2014; dated Feb. 28, 2017.
Marcetich, Adam, "Notice of Allowance", U.S. Appl. No. 14/793,455, filed Jul. 7, 2015; dated Jul. 20, 2017.
Marcetich, Adam M., "Final OA", U.S. Appl. No. 14/165,044, filed Jan. 27, 2014; Mailed Aug. 11, 2016.
Marcitech, Adam, "NonFinal OA", U.S. Appl. No. 14/793,455, filed Jul. 7, 2015; Mailed May 3, 2017.
Medline, "Medline Urologists Better by Design", Article; published 2008.
Ortega, Rafael et al., "Female Urethral Catheterization", N. Engl. J. Med vol. 358:e15; published 2008.
Pass, Natalie, "Final OA", U.S. Appl. No. 13/153,265, filed Jun. 3, 2011; Mailed Jul. 12, 2013.
Pass, Natalie, "NonFinal OA", U.S. Appl. No. 13/153,265, filed Jun. 3, 2011; Mailed Mar. 5, 2013.
Poon, Robert, "Appeal Decision", U.S. Appl. No. 12/647,515, filed Dec. 27, 2009; Mailed Jan. 19, 2018.
Poon, Robert, "Appeal Decision", U.S. Appl. No. 13/153,300, filed Jun. 3, 2011; Mailed Oct. 12, 2016.
Poon, Robert, "Appeal Decision", U.S. Appl. No. 13/374,509, filed Dec. 30, 2011; Mailed Oct. 24, 2016.
Poon, Robert, "Appeal Decision", U.S. Appl. No. 14/265,920, filed Apr. 30, 2014; Mailed Aug. 1, 2018.
Poon, Robert, "Final OA", U.S. Appl. No. 12/647,515, filed Dec. 27, 2009; Mailed Apr. 7, 2015.
Poon, Robert, "Final OA", U.S. Appl. No. 12/647,515, filed Dec. 27, 2009; Mailed May 13, 2013.
Poon, Robert, "Final OA", U.S. Appl. No. 12/846,675, filed Jul. 29, 2010; Mailed Dec. 18, 2013.
Poon, Robert, "Final OA", U.S. Appl. No. 13/153,300, filed Jun. 3, 2011; Mailed Aug. 6, 2013.
Poon, Robert, "Final OA", U.S. Appl. No. 13/374,509, filed Dec. 30, 2011; Mailed Aug. 6, 2013.
Poon, Robert, "Final OA", U.S. Appl. No. 14/265,909, filed Apr. 30, 2014; Mailed Jan. 10, 2017.
Poon, Robert, "Final OA", U.S. Appl. No. 14/265,909, filed Apr. 30, 2015; Mailed Oct. 5, 2015.
Poon, Robert, "Final OA", U.S. Appl. No. 14/265,920, filed Apr. 30, 2014; Mailed Oct. 2, 2015.
Poon, Robert, "Final OA", U.S. Appl. No. 14/718,912, filed May 21, 2015; Mailed Jan. 5, 2016.
Poon, Robert, "Final OA", U.S. Appl. No. 15/067,903, filed Mar. 11, 2016; Mailed Jan. 13, 2017.
Poon, Robert, "Final Office Action", U.S. Appl. No. 12/495,148, filed Jun. 30, 2009, dated Mar. 3, 2011.
Poon, Robert, "Final Office Action", U.S. Appl. No. 12/495,148, filed Jun. 30, 2009; dated Jul. 31, 2013.
Poon, Robert, "Final Office Action", U.S. Appl. No. 12/846,675, filed Jul. 29, 2010; dated Sep. 26, 2012.
Poon, Robert, "Final Office Action", U.S. Appl. No. 14/718,912, filed May 21, 2015; dated Jan. 5, 2016.
Poon, Robert, "NonFinal OA", U.S. Appl. No. 12/495,148, filed Jun. 30, 2009; Mailed Oct. 4, 2012.
Poon, Robert, "NonFinal OA", U.S. Appl. No. 12/647,515, filed Dec. 27, 2009; Mailed Dec. 18, 2013.
Poon, Robert, "NonFinal OA", U.S. Appl. No. 12/846,675, filed Jul. 29, 2010; Mailed Sep. 10, 2013.
Poon, Robert, "NonFinal OA", U.S. Appl. No. 14/265,909, filed Apr. 30, 2014; Mailed Sep. 12, 2016.
Poon, Robert, "NonFinal OA", U.S. Appl. No. 14/265,909, filed Apr. 30, 2014; Mailed Dec. 31, 2014.
Poon, Robert, "NonFinal OA", U.S. Appl. No. 14/265,920, filed Apr. 30, 2014; Mailed Dec. 30, 2014.
Poon, Robert, "NonFinal OA", U.S. Appl. No. 14/718,792, filed May 21, 2015; Mailed Nov. 19, 2015.
Poon, Robert, "NonFinal OA", U.S. Appl. No. 15/067,903, filed Mar. 11, 2016; Mailed Jun. 30, 2016.
Poon, Robert, "NonFinal OA", U.S. Appl. No. 15/803,383, filed Nov. 3, 2017; Mailed Mar. 7, 2018.
Poon, Robert, "NonFinal OA", U.S. Appl. No. 15/804,520, filed Nov. 6, 2017; Mailed Jan. 19, 2018.
Poon, Robert, "Non-Final OA", U.S. Appl. No. 14/265,909, filed Apr. 30, 2014; Mailed Aug. 24, 2017.
Poon, Robert, "NonFinal Office Action", U.S. Appl. No. 15/703,514, filed Sep. 13, 2017; dated Jun. 22, 2018.
Poon, Robert, "NonFinal Office Action", U.S. Appl. No. 12/647,515, filed Dec. 27, 2009; dated Jun. 28, 2012.
Poon, Robert, "NonFinal Office Action", U.S. Appl. No. 12/846,675, filed Jul. 29, 2010; dated Dec. 22, 2011.
Poon, Robert, "NonFinal Office Action", U.S. Appl. No. 13/153,300, filed Jun. 3, 2011; dated Oct. 1, 2012.
Poon, Robert, "NonFinal Office Action", U.S. Appl. No. 13/374,509, filed Dec. 30, 2011; dated Oct. 2, 2012.
Poon, Robert, "NonFinal Office Action", U.S. Appl. No. 15/804,520, filed Nov. 6, 2017; dated Jun. 6, 2018.
Poon, Robert, "Non-Final Office Action", U.S. Appl. No. 12/495,148, filed Jun. 30, 2009; first inventor: Jennifer E. Tomes; dated Aug. 4, 2010.
Poon, Robert, "Notice of Allowance", U.S. Appl. No. 12/495,148, filed Jun. 30, 2009; dated Nov. 20, 2013.
Poon, Robert, "Notice of Allowance", U.S. Appl. No. 12/846,675, filed Jul. 29, 2010; dated Apr. 30, 2014.
Poon, Robert, "Notice of Allowance", U.S. Appl. No. 14/718,792, filed May 21, 2015; dated Feb. 2, 2016.
Poon, Robert, "Notice of Allowance", U.S. Appl. No. 14/265,909, filed Apr. 30, 2014; dated Oct. 2, 2017.
Poon, Robert, "Notice of allowance", U.S. Appl. No. 15/067,903, filed Mar. 11, 2016; dated Aug. 23, 2017.
Poon, Robert, "Restriction Requirement", U.S. Appl. No. 12/647,515, filed Dec. 27, 2009; dated May 23, 2012.
Pothier, Andrew, "NonFinal OA", Canadian Application No. 2,837,289; Mailed Feb. 14, 2018.
Pothier, Andrew, "NonFinal Office Action", Canadian Patent Application No. 2,822,905; Reference No. 15468-P44352CA00 (10055U CIP4 CA); dated Aug. 31, 2018.
Pothier, Andrew, "Non-Final Office Action", Canadian Application No. 2,822,905; File No. 15468-P44352CA00; dated Dec. 18, 2017.
Pothier, Andrew, "Office Action", Canadian Application No. 2,822,905; Reference No. 15468-P44352CA00; dated May 1, 2017.
Prange, Sharon M., "Response to First Office Action", U.S. Appl. No. 12/004,796, filed Dec. 21, 2007; dated Oct. 28, 2009.
Schultz, Ottmar, "Extended European Search Report", EP Application No. 16177903.8-1501; Filed Jun. 30, 2009; dated Oct. 27, 2016.

(56) References Cited

OTHER PUBLICATIONS

Thomsen, Todd, "Male Urethral Catheterization", N. Engl. J. Med vol. 354:e22; Published 2006.
Vasat, Peter, "NonFinal OA", U.S. Appl. No. 12/785,064, filed May 21, 2010; Mailed Feb. 9, 2018.
Vasat, Peter, "Notice of Allowance", U.S. Appl. No. 12/785,064, filed May 21, 2010; dated Sep. 12, 2016.
Yuan, Minqiang, "Non-Final Office Action", Chinese Application No. 200920267201.2, dated Sep. 9, 2010.
Yuan, Minquiang, "Non-Final Office Action", Chinese Application No. 200920267201.2, dated Jun. 4, 2010.
*Medline Industries Inc.* vs *C.R. Bard, Inc.*; Exhibit 1 to Declaration of Karl L. Leinsing in Support of Bard's Rebuttal on Claim Construction; Civil Action No. 1:16-cv-03529; Judge Sharon Johnson Coleman; Filed Jan. 12, 2018.
*Medline Industries Inc.* vs *C.R. Bard, Inc.*; Exhibit A to Declaration of Bnan Eutermoser in Support of Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard, Inc.*; Exhibit A to Declaration of Dylan J Raife in Support of Bard's Reply Claim Construction Brief; Civil Action No. t:14-cv-03618: Judge John Z. Lee; Filed Aug. 15, 2016.
*Medline Industries Inc.* vs *C.R. Bard, Inc.*; Exhibit F to C.R. Bard's LPR 2.3 Contentions; Civil Action No. 1.17-cv-7216; Judge Sara L. Ellis; Filed Jan. 16, 2018.
*Medline Industries Inc.* vs *C.R. Bard. Inc.*; Exhibit 4 to Declaration of Richard Meyst re Claim Construction; Civil Action No. 1:16-cv-03529: Judge Sharon Johnson Coleman; Filed Dec. 9, 2016.
*Medline Industries Inc.* vs *C.R. Bard. Inc.*; Exhibit C to Declaration of Nicole Smith in Support of Bard Reply to Claim Construction Brief; Civil Action No. 1.16-cv-03529; Judge Sharon Johnson Coleman. Filed Jan. 12. 2018.
*Medline Industries Inc.* vs *C.R. Bard. Inc.*; Exhibit 3 to Declaration of Richard Meyst re Claim Construction; Civil Action No. 1:16-cv-03529: Judge Sharon Johnson Coleman. Filed Dec. 9, 2016.
*Medline Industries Inc.* vs *C.R. Bard. Inc.*; Exhibit C to Declaration of Nicole Smith in Support of Bard Reply to Medline Claim Construction Brief; Civil Action No. 116-cv-03529; Judge Sharon Johnson Coleman; Filed Jan. 27, 2017.
*Medline Industries Inc.* vs *C.R. Bard. Inc.*; Exhibit F to Declaration of Brian Eutermoser in Support of Medline Response to Bard Opening Claim Construction; Civil Action No. 1:16-cv-03529; Judge Sharon Johnson Coleman: Filed Dec. 9, 2016.
*Medline Industries Inc.* vs *C.R. Bard, Inc.*; Exhibit E to Declaration of Nicole Smith in Support of Bard Reply lo Claim Construction Brief; Civil Action No. 1.16-cv-03529. Judge Sharon Johnson Coleman. Filed Jan. 12, 2018.
*Medline Industries Inc.* vs *C.R. Bard, Inc.*; Exhibit A (List of Invalidating Prior Art) to C R. Bard's LPR 2 3 Contentions; Civil Action No. t:17-cv-7216; Judge Sara L. Ellis; Filed Jan. 16, 2018.
*Medline Industries Inc.* vs *C R. Bard, Inc.*; Exhibit E to Declaration of Dylan Raife in Support of Motion for Leave to Add Counterclaims; Civil Action No. 1:17-cv-7216; Judge Sara L. Ellis; Filed Feb. 27, 2018.
*Medline Industries Inc.* vs *C.R. Bard, Inc.*; Exhibit A to Declaration of Nicole M. Smith; Civil Action No. 1:14-cv-03618; Judge John Z. Lee: Filed Jun. 4, 2016.
*Medline Industries Inc.* vs *C R. Bard, Inc.*; C.R. Bard's LPR 2 3 Contentions; Civil Action No. 1:17-cv-7216, Judge Sara L. Ellis; Filed Jan. 16, 2018.
*Medline Industries Inc.* vs *C R. Bard, Inc.*; Declaration of Nicole M Smith in Support of Bard Opening Claim Construction Brief; Civil Action No. 1:14-cv-03618: Judge John Z. Lee; Filed Jun. 4, 2016.
*Medline Industries Inc.* vs *C R. Bard, Inc.*; Exhibit B to Declaration of Dylan Raife in Support of Motion for Leave to Add Counterclaims; Civil Action No. 1:17-cv7216; Judge Sara L. Ellis; Filed Feb. 27, 2018.

*Medline Industries Inc.* vs *C R. Bard, Inc.*; Exhibit D to Declaration of Dylan Raife in Support of Motion for Leave to Add Counterclaims; Civil Action No. 1:17-cv-7216; Judge Sara L. Ellis: Filed Feb. 27, 2018.
*Medline Industries Inc.* vs *C.R. Bard, Inc.*; Exhibit G to Declaration of Nicole M. Smith; Civil Action No. 1:14-cv-03618; Judge John Z, Lee; Filed Jun. 4, 2016.
*Medline Industries Inc.* vs *C.R. Bard, Inc.*; Exhibit H to Declaration of Nicole M. Smith; Civil Action No. 1:14-cv-03618; Judge John Z. Lee; Filed Jun. 4, 2016.
*Medline Industries Inc.* vs *C R. Bard, Inc.*; Exhibit A—C R. Bards Second Amended Answer to Second Amended Complaint: Civil Action No. 1:17-cv-7216; Judge Sara L Ellis; Filed Feb. 27, 2018.
*Medline Industries Inc.* vs *C.R. Bard, Inc.*; Declaration of Barbara Weintraub re Claim Construction; Civil Action No. 1:16-cv-03529; Judge Sharon Johnson Coleman; Filed Dec. 22, 2017.
*Medline Industries Inc.* vs *C.R. Bard, Inc.*; Declaration of Dylan J Raife in Support of Bard Opening Claim Construction Brief; Civil Action No. 1:16-cv-03529; Judge Sharon Johnson Coleman; Filed Nov. 17, 2017.
*Medline Industries Inc.* vs *C.R. Bard, Inc.*; Declaration of Nicole Smith in Support of Bard Reply to Medline Claim Construction Brief; Civil Action No. 1:16-cv-03529; Judge Sharon Johnson Coleman; Filed Jan. 27, 2017.
*Medline Industries Inc.* vs *C.R. Bard, Inc.*; Exhibit 1 to Declaration of Richard Meyst re Claim Construction; Civil Action No. 1:16-cv-03529; Judge Sharon Johnson Coleman; Filed Dec. 9, 2016.
*Medline Industries Inc.* vs *C.R. Bard, Inc.*; Exhibit 2 lo Declaration of Richard Meyst re Claim Construction; Civil Action No. 1:16-cv-03529; Judge Sharon Johnson Coleman; Filed Dec. 9, 2016.
*Medline Industries Inc.* vs *C.R. Bard, Inc.*; Exhibit 7 to Declaration of Richard Meyst Regarding Claim Construction: Civil Action No. 1:14-cv-03618; Judge John Z. Lee; Filed Jul. 8, 2016.
*Medline Industries Inc.* vs *C.R. Bard, Inc.*; Exhibit A to Declaration of Dylan J Raife in Support of Bard Opening Claim Construction Brief; Civil Action No. 1;16-cv-03529; Judge Sharon Johnson Coleman; Filed Nov. 11, 2016.
*Medline Industries Inc.* vs *C.R. Bard, Inc.*; Exhibit A to Declaration of Kevin A. Lake. Civil Action No. 1:14-cv-03618; Judge John Z. Lee; Filed Jul. 8, 2016.
*Medline Industries Inc.* vs *C.R. Bard, Inc.*; Exhibit B to Declaration of Brian Eutermoser in Support of Medline Response to Bard Opening Claim Construction; Civil Action No. 1:16-cv-03529: Judge Sharon Johnson Coleman: Filed Dec. 9, 2016.
*Medline Industries Inc.* vs *C.R. Bard, Inc.*; Exhibit F to Declaration of Dylan J. Raife in Support of Bard Opening Claim Construction Brief, Civil Action No. 1:16-cv-03529; Judge Sharon Johnson Coleman; Filed Nov. 11, 2016.
*Medline Industries Inc.* vs *C.R. Bard, Inc.*; Exhibit F to Declaration of Nicole Smith in Support of Bard Reply to Medline Claim Construction Brief; Civil Action No. 1:16-cv-03529; Judge Sharon Johnson Coleman; Filed Jan. 27, 2017.
*Medline Industries Inc.* vs *C.R. Bard, Inc.*; Exhibit H to Declaration of Kevin A. Lake; Civil Action No. 1:14-cv-03618: Judge John Z. Lee; Filed Jul. 8, 2016.
*Medline Industries Inc.* vs *C.R. Bard, Inc.*; Bard Opening Claim Construction Brief; Civil Action No. 1:16-cv-03529; Judge Sharon Johnson Coleman; Filed Nov. 11, 2016.
*Medline Industries Inc.* vs *C.R. Bard, Inc.*; Declaration of Dylan J Raife in Support of Bard's Reply Claim Construction Brief: Civil Action No. I:14-cv-03518; Judge John Z. Lee; Filed Aug. 15, 2016.
*Medline Industries Inc.* vs *C.R. Bard, Inc.*; Exhibit 1 to Declaration of Dylan J. Raife in Support of Bard Opening Claim Construction Brief; Civil Action No. 1:16-cv-03529; Judge Sharon Johnson Coleman; Filed Nov. 11, 2016.
*Medline Industries Inc* vs *C.R. Bard, Inc.*; Exhibit 10 to Declaration of Richard Meyst Regarding Claim Construction: Civil Action No. 1:14-cv-03618; Judge John Z. Lee; Filed Jul. 8, 2016.
*Medline Industries Inc.* vs *C.R. Bard, Inc.*; Exhibit 2 to Declaration of Brian Eutermoser in Support of Medline Surreply: Civil Action No. 1:14-cv-03618; Judge John Z. Lee; Filed Sep. 7, 2016.

(56) References Cited

OTHER PUBLICATIONS

*Medline Industries Inc.* vs *C.R. Bard, Inc.*; Exhibit C to Declaration of Dylan J Raife in Support of Bard Opening Claim Construction Brief; Civil Action No. 1:16-cv-03529; Judge Sharon Johnson Coleman: Filed Nov. 11, 2016.
*Medline Industries Inc.* vs *C.R. Bard, Inc.*; Exhibit E to Declaration of Nicole Smith in Support of Bard Reply to Medline Claim Construction Brief; Civil Action No. 1:16-cv-03529; Judge Sharon Johnson Coleman; Filed Jan. 27, 2017.
*Medline Industries Inc.* vs *C.R. Bard, Inc.*; Exhibit I to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard, Inc.*; Exhibit I to Declaration of Nicole M. Smith, Civil Action No. 1:14-cv-03618: Judge John Z. Lee; Filed Jun. 4, 2016.
*Medline Industries Inc.* vs *C.R. Bard, Inc.*; Bard Reply to Medline Claim Construction Brief; Civil Action No. 1 16-cv-03529; Judge Sharon Johnson Coleman; Filed Jan. 27, 2017.
*Medline Industries Inc.* vs *C.R. Bard, Inc.*; C. R. Bard's Reply in Support of Claim Construction Brief; Civil Action No. 1.14-cv-03618, Judge John Z. Lee; Filed Aug. 15, 2016.
*Medline Industries Inc.* vs *C.R. Bard, Inc.*; Declaration of Karl L Leinsing in Support of Bard's Rebuttal on Claim Construction; Civil Action No. 1:16-CV-03529; Judge Sharon Johnson Coleman; Filed Jan. 12, 2018.
*Medline Industries Inc.* vs *C.R. Bard, Inc.*; Declaration of Karl L. Leinsing in Support of Bard's Rebuttal on Claim Construction; Civil Action No. 1.14-cv-03618. Judge John Z. Lee; Filed Aug. 15, 2016.
*Medline Industries Inc.* vs *C.R. Bard, Inc.*; Declaration of Richard Meyst re Claim Construction; Civil Action No. 1.16-cv-03529. Judge Sharon Johnson Coleman; Filed Dec. 9, 2016.
*Medline Industries Inc.* vs *C.R. Bard, Inc.*; Exhibit 1 to Declaration of Karl L Leinsing in Support of Bard's Rebuttal on Claim Construction; Civil Action No. 1.14-cv-03618; Judge John Z. Lee, Filed Aug. 15, 2016.
*Medline Industries Inc.* vs *C.R. Bard, Inc.*; Exhibit 1 to Declaration of Karl R Leinsing in Support of Bard Reply to Medline Claim Construction Brief; Civil Action No. 1:16-cv-03529; Judge Sharon Johnson Coleman; Filed Jan. 27, 2017.
*Medline Industries Inc.* vs *C.R. Bard, Inc.*; Exhibit 3 to Declaration of Richard Meyst Regarding Claim Construction; Civil Action No. 1:14-cv-03618; Judge John Z. Lee, Filed Jul. 8, 2016.
*Medline Industries Inc.* vs *C.R. Bard, Inc.*; Exhibit 4 to Declaration of Richard Meyst Regarding Claim Construction; Civil Action No. 1:14-cv-03618; Judge John Z. Lee. Filed Jul. 8, 2016.
*Medline Industries Inc.* vs *C.R. Bard, Inc.*; Exhibit A to Declaration of Barbara Weintraub re Claim Construction; Civil Action No. 1:16-cv-03529; Judge Sharon Johnson Coleman. Filed Dec. 9, 2016.
*Medline Industries Inc.* vs *C.R. Bard, Inc.*; Exhibit B to Declaration of Nicole Smith in Support of Bard Reply to Claim Construction Brief; Civil Action No. 1;16-cv-03529. Judge Sharon Johnson Coleman. Filed Jan. 12, 2018.
*Medline Industries Inc.* vs *C.R. Bard, Inc.*; Exhibit B to Declaration of Dylan J Raife in Support of Bard's Reply Claim Construction Brief; Civil Action No. 1:14-cv-03618; Judge John Z. Lee; Filed Aug. 15, 2016.
*Medline Industries Inc.* vs *C.R. Bard, Inc.*; Exhibit C to Declaration of Dylan J Raife in Support of Bard's Reply Claim Construction Brief; Civil Action No. 1:14-cv 03618; Judge John Z. Lee; Filed Aug. 15, 2016.
*Medline Industries Inc.* vs *C.R. Bard, Inc.*; Exhibit D to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard, Inc.*; Exhibit D to Declaration of Dylan J Raife in Support of Bard's Reply Claim Construction Brief: Civil Action No. 1.14-cv-03618; Judge John Z. Lee. Filed Aug. 15, 2016.
*Medline Industries Inc.* vs *C.R. Bard, Inc.*; Exhibit D to Declaration of Nicole Smith in Support of Bard Reply to Medline Claim Construction Brief; Civil Action No. 1.16-cv-03529; Judge Sharon Johnson Coleman; Filed Jan. 27, 2017.
*Medline Industries Inc.* vs *C.R. Bard, Inc.*; Exhibit E to Declaration of Kevin A. Lake; Civil Action No. 1:14-cv-03618, Judge John Z. Lee; Filed Jul. 8, 2016.
*Medline Industries Inc.* vs *C.R. Bard, Inc.*; Exhibit F lo Declaration of Kevin A Lake: Civil Action No. 1:14-cv-03618. Judge John Z. Lee; Filed Jul. 8, 2016.
*Medline Industries Inc.* vs *C.R. Bard, Inc.*; Exhibit F to Declaration of Dylan J. Raife in Support of Bard's Reply Claim Construction Brief; Civil Action No. 1. I4-cv-03618; Judge John Z. Lee, Filed Aug. 15, 2016.
*Medline Industries Inc.* vs *C.R. Bard, Inc.*; Exhibit G to Declaration of Kevin A. Lake; Civil Action No. 1:14-cv-03618. Judge John Z. Lee; Filed Jul. 8, 2016.
*Medline Industries Inc.* vs *C.R. Bard, Inc.*; Exhibit G to Declaration of Nicole Smith in Support ofBard Reply to Medline Claim Construction Brief: Civil Action No. 1:16-cv-03529: Judge Sharon Johnson Coleman; Filed Jan. 27, 2017.
*Medline Industries Inc.* vs *C.R. Bard, Inc.*; Exhibit H to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard, Inc.*; Exhibit H to Declaration of Dylan J. Raife in Support of Bard Opening Claim Construction Brief. Civil Action Mo. 1:16-cv-Q3529; Judge Sharon Johnson Coleman; Filed Nov. 11, 2016.
*Medline Industries Inc.* vs *C.R. Bard, Inc.*; Exhibit I to Declaration of Kevin A. Lake; Civil Action No. 1.14-sv-03618; Judge John Z. Lee; Filed Jul. 8, 2016.
*Medline Industries Inc.* vs *C.R. Bard, Inc.*; Exhibit N to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard, Inc.*; Medline Memo of Law re Expert Testimony in Claim Construction Proceedings; Civil Action No. 1:14-cv-03618; Judge John Z. Lee. Filed Jan. 25, 2017.
*Medline Industries Inc.* vs *C.R. Bard, Inc.*; Medline Surreply to Claim Construction Brief; Civil Action No. 1:14-CV-Q3618: Judge John Z. Lee; Filed Sep. 7, 2016.
*Medline Industries Inc.* vs *C.R. Bard, Inc.*; Transcript of Deposition of Richard Meyst; Civil Action No. 1:16-W-03529. Jan. 20, 2017.
*Medline Industries Inc.* vs *C.R. Bard, Inc.*; Exhibit G to C.R. Bard's LPR 2.3 Contentions; Civil Action No. 1:17-cv-7216; Judge Sara L Ellis; Filed Jan. 16, 2018.
*Medline Industries Inc.* vs *C.R. Bard, Inc.*; Exhibit 3 to C.R. Bard's LPR 2.3 Contentions; Civil Action No. 1:17-Cv-7216; Judge Sara L Ellis; Filed Jan. 16, 2018.
*Medline Industries Inc.* vs *C.R. Bard, Inc.*; Exhibit C to C.R. Bard's LPR 2.3 Contentions; Civil Action No. 1:17-cv-7216; Judge Sara L. Ellis; Filed Jan. 16, 2018.
*Medline Industries Inc.* vs *C.R. Bard, Inc.*; Exhibit D to C.R. Bard's LPR 2.3 Contentions; Civil Action No. 1:17-cv-7216; Judge Sara L. Ellis; Filed Jan. 16, 2018.
*Medline Industries Inc.* vs *C.R. Bard, Inc.*; Exhibit E to C R. Bard's LPR 2.3 Contentions; Civil Action No. 1;17-cv-7216; Judge Sara L. Ellis; Filed Jan. 16, 2018.
*Medline Industries Inc.* vs *C.R. Bard. Inc.*; Exhibit H to C.R. Bard's LPR 2.3 Contentions. Civil Action No. 1:17-CV-7216; Judge Sara L. Ellis: Filed Jan. 16, 2018.
*Medline Industries Inc.* vs *C.R. Bard. Inc.*; Declaration of Bnan Eutermoser in Support of Medline Surreply. Civil Action No. 1:14-cv-03618, Judge John Z. Lee; Filed Sep. 7, 2016.
*Medline Industries Inc.* vs *C.R. Bard. Inc.*; Exhibit 8 lo Declaration of Richard Meyst Regarding Claim Construction: Civil Action No. 1:14-cv-03618: Judge John Z. Lee: Filed Jul. 8, 2016.
*Medline Industries Inc.* vs *C.R. Bard. Inc.*; Exhibit A to Declaration of Barbara Weintraub Regarding Claim Construction: Civil Action No. 1.14-cv-03618. Judge John Z. Lee; Filed Jul. 8, 2016.
*Medline Industries Inc.* vs *C.R. Bard. Inc.*; Exhibit A to Declaration of Nicole Smith in Support of Bard Reply lo Medline Claim

(56) References Cited

OTHER PUBLICATIONS

Construction Brief; Civil Action No. 1.16-cv-03529; Judge Sharon Johnson Coleman; Filed Jan. 27, 2017.
*Medline Industries Inc.* vs *C.R. Bard. Inc.*; Exhibit B to Declaration of Dylan J Raife in Support of Bard Opening Claim Construction Brief; Civil Action No. 1:16-cv-03529; Judge Sharon Johnson Coleman; Filed Nov. 11, 2016.
*Medline Industries Inc.* vs *C.R. Bard. Inc.*; Exhibit E to Declaration of Dylan J Raife in Support of Bard's Reply Claim Construction Brief; Civil Action No. 1.14-cv-03618; Judge John Z. Lee, Filed Aug. 15, 2016.
*Medline Industries Inc.* vs *C.R. Bard. Inc.*; Declaration of Richard Meyst Regarding Claim Construction; Civil Action No. 1:14-cv-03618; Judge John Z. Lee; Filed Jul. 8, 2016.
*Medline Industries Inc.* vs *C.R. Bard. Inc.*; Exhibit 11 to Declaration of Richard Meyst re Claim Construction: Civil Action No. 1:16-cv-03529; Judge Sharon Johnson Coleman; Filed Dec. 9, 2016.
*Medline Industries Inc.* vs *C.R. Bard. Inc.*; Exhibit A to Declaration of Richard Meyst Regarding Claim Construction; Civil Action No. 1:14-cv-03618; Judge John Z. Lee; Filed Jul. 8, 2016.
*Medline Industries Inc.* vs *C.R. Bard. Inc.*; Medline Motion to Supplement Record on Claim Construction with Leinsing Testimony; Civil Action No. 1:14-w-03618; Judge John Z. Lee; Filed Mar. 23, 2017.
*Medline Industries Inc.* vs *C.R. Bard. Inc.*; Bard Reply Claim Construction Brief; Civil Action No. 1:16-cv-03529; Judge Sharon Johnson Coleman; Filed Jan. 12, 2018.
*Medline Industries Inc.* vs *C.R. Bard. Inc.*; Bard Response to Memo of Law re Expert Testimony in Claim Construction Proceedings; Civil Action No. 1:14-cv-03618; Judge John Z. Lee. Filed Feb. 8, 2017.
*Medline Industries Inc.* vs *C.R. Bard. Inc.*; Declaration of Brian Eutermoser in Support of Medline Response to Bard Opening Claim Construction Brief. Civil Action No. 1:16-cv-03529; Judge Sharon Johnson Coleman; Filed Dec. 22, 2017.
*Medline Industries Inc.* vs *C.R. Bard. Inc.*; Declaration of Karl R. Leinsing in Support of Bard Reply to Medline Claim Construction Brief; Civil Action No. 1:16-cv-03529; Judge Sharon Johnson Coleman; Filed Jan. 27, 2017.
*Medline Industries Inc.* vs *C.R. Bard. Inc.*; Exhibit 3 to Declaration of Peter Sauer in Support of Medline's Motion to Supplement Record; Civil Action No. 1:14-cv-03618: Judge John Z. Lee. Filed Mar. 23, 2017.
*Medline Industries Inc.* vs *C.R. Bard. Inc.*; Exhibit 8 to Declaration of Richard Meyst re Claim Construction; Civil Action No. 1:16-cv-03529; Judge Sharon Johnson Coleman; Filed Dec. 9, 2016.
*Medline Industries Inc.* vs *C.R. Bard. Inc.*; Exhibit C to Declaration of Kevin A. Lake; Civil Action No. 1 14-cv-03618. Judge John Z. Lee; Filed Jul. 8, 2016.
*Medline Industries Inc.* vs *C.R. Bard. Inc.*; Exhibit G to Declaration of Dylan J. Raife in Support of Bard Opening Claim Construction Brief, Civil Action No. 1:16-cv-03529; Judge Sharon Johnson Coleman; Filed Nov. 17, 2017.
*Medline Industries Inc.* vs *C.R. Bard. Inc.*; Exhibit G to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard. Inc.*; Exhibit H to Declaration of Dylan J Raife in Support of Bard Opening Claim Construction Brief, Civil Action No. 1:16-cv-03529; Judge Sharon Johnson Coleman; Filed Nov. 17, 2017.
*Medline Industries Inc.* vs *C.R. Bard. Inc.*; Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard. Inc.*; Transcript of Deposition of Barbara A Weintraub; Civil Action Mo. 1:16-cv-03529; Jan. 20, 2017.
*Medline Industries Inc.* vs *C.R. Bard. Inc.*; Transcript of Deposition of Karl Leinsing; Civil Action No. 1:16-cv-03529; Feb. 17, 2017.
*Medline Industries Inc.* vs *C.R. Bard, Inc.*; Exhibit 9 to Declaration of Richard Meyst re Claim Construction; Civil Action No. 1:16-cv-03529; Judge Sharon Johnson Coleman; Filed Dec. 9, 2016.
*Medline Industries Inc.* vs *C.R. Bard, Inc.*; Bard Response to Medline Surreply re Claim Construction; Civil Action No. 1:14-cv-03618; Judge John Z. Lee; Filed Sep. 13, 2016.
*Medline Industries Inc.* vs *C.R. Bard, Inc.*; Exhibit 2 to Declaration of Karl L. Leinsing in Support of Bard's Rebuttal on Claim Construction: Civil Action No. 1:14-cv-03618; Judge John Z. Lee; Filed Aug. 15, 2016.
*Medline Industries Inc.* vs *C.R. Bard, Inc.*; Exhibit B to Declaration of Kevin A. Lake. Civil Action No. 1:14-cv-03618; Judge John Z. Lee; Filed Jul. 8, 2016.
*Medline Industries Inc.* vs *C.R. Bard, Inc.*; Exhibit D to Declaration of Nicole Smith in Support of Bard Reply to Claim Construction Brief; Civil Action No. 116-cv-03529; Judge Sharon Johnson Coleman. Filed Jan. 12, 2018.
*Medline Industries Inc.* vs *C.R. Bard, Inc.*; Exhibit J to Declaration of Brian Eutermoser in Support of Medline Response to Bard Opening Claim Construction; Civii Action No. 1:16-cv-03529: Judge Sharon Johnson Coleman; Filed Dec. 9, 2016.
*Medline Industries Inc.* vs *C.R. Bard, Inc.*; Exhibit K to Declaration of Bnan Eutermoser in Support of Medline Response to Bard Opening Claim Construction; Civil Action No. 1:16-cv-03529: Judge Sharon Johnson Coleman; Filed Dec. 9, 2016.
*Medline Industries Inc.* vs *C.R. Bard, Inc.*; Exhibit 1 to Declaration of Peter Sauer in Support of Medline's Motion to Supplement Record; Civil Action No. 1:14-cv-03618; Judge John Z. Lee; Filed Mar. 23, 2017.
*Medline Industries Inc.* vs *C.R. Bard, Inc.*; Exhibit 9 to Declaration of Richard Meyst Regarding Claim Construction; Civil Action No. 1:14-cv-03618; Judge John Z. Lee; Filed Jul. 8, 2016.
*Medline Industries Inc.* vs *C.R. Bard, Inc.*; Exhibit L to Declaration of Brian Eutermoser in Support of Medline Response to Bard Opening Claim Construction; Civil Action No. 1:16-cv-03529: Judge Sharon Johnson Coleman: Filed Dec. 9, 2016.
*Medline Industries Inc.* vs *C.R. Bard, Inc.*; Medline Response to Bard Claim Construction Brief. Civil Action No. 1:14-cv-03618: Judge John Z. Lee; Filed Jul. 8, 2016.
*Medline Industries Inc.* vs *C.R. Bard, Inc.*: Exhibit 2 to C.R. Bard's LPR 2.3 Contentions; Civil Action No. 117-CV-7216; Judge Sara L Ellis; Filed Jan. 16, 2018.
*Medline Industries Inc.* vs *C.R. Bard, Inc.*; Declaration of Barbara Weintraub re Claim Construction: Civil Action No. 1.16-cv-03529. Judge Sharon Johnson Coleman; Filed Dec. 9, 2016.
*Medline Industries Inc.* vs *C.R. Bard, Inc.*; Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard, Inc.*; Declaration of Nicole Smith in Support of Bard Reply to Claim Construction Brief; Civil Action No. 1:16-cv-03529; Judge Sharon Johnson Coleman; Filed Jan. 12, 2018.
*Medline Industries Inc.* vs *C.R. Bard, Inc.*; Exhibit 10 lo Declaration of Richard Meyst re Claim Construction; Civil Action No. 1:16-cv-03529; Judge Sharon Johnson Coleman; Filed Dec. 9, 2016.
*Medline Industries Inc.* vs *C.R. Bard, Inc.*; Exhibit 2 to Declaration of Peter Sauer in Support of Medline's Motion to Supplement Record; Civil Action No. 1:14-cv-03618; Judge John Z. Lee. Filed Mar. 23, 2017.
*Medline Industries Inc.* vs *C.R. Bard, Inc.*; Exhibit 5 to Declaration of Richard Meyst re Claim Construction: Civil Action No. 1:16-cv-03529; Judge Sharon Johnson Coleman, Filed Dec. 9, 2016.
*Medline Industries Inc.* vs *C.R. Bard, Inc.*; Exhibit 6 to Declaration of Richard Meyst re Claim Construction; Civil Action No. 1:16-cv-03529; Judge Sharon Johnson Coleman. Filed Dec. 9, 2016.
*Medline Industries Inc.* vs *C.R. Bard, Inc.*; Exhibit 7 to Declaration of Richard Meyst re Claim Construction; Civil Action No. 1:16-cv-03529; Judge Sharon Johnson Coleman; Filed Dec. 9, 2016.
*Medline Industries Inc.* vs *C.R. Bard, Inc.*; Exhibit C to Declaration of Bnan Eutermoser in Support of Medline Response to Bard Opening Claim Construction; Civil Action No. 1:16-cv-03529; Judge Sharon Johnson Coleman; Filed Dec. 9, 2016.

(56) References Cited

OTHER PUBLICATIONS

*Medline Industries Inc.* vs *C.R. Bard, Inc.*; Exhibit E to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard, Inc.*; Exhibit M to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc.* vs *C.R. Bard. Inc.*; Exhibit 2 to Declaration of Richard Meyst Regarding Claim Construction: Civil Action No. 1:14-cv-03618; Judge John Z. Lee. Filed Jul. 8, 2016.
*Medline Industries Inc.* vs *C.R. Bard. Inc.*; Exhibit 5 to Declaration of Richard Meyst Regarding Claim Construction; Civil Action No. 1:14-cv-03618; Judge John Z. Lee. Filed Jul. 8, 2016.
*Medline Industries Inc.* vs *C.R. Bard. Inc.*; Exhibit 6 to Declaration of Richard Meyst Regarding Claim Construction; Civil Action No. 1:14-cv-03618; Judge John Z. Lee. Filed Jul. 8, 2016.
*Medline Industries Inc.* vs *C.R. Bard. Inc.*; Medline Response to Bard Opening Claim Construction Brief; Civil Action No. 1:16-cv-03529; Judge Sharon Johnson Coleman; Filed Dec. 22, 2017.
*Medline Industries Inc.* vs *OR. Bard, Inc.*; Exhibit E to Declaration of Dylan J Raife in Support of Bard Opening Claim Construction Brief; Civil Action No. 1:16-cv-03529; Judge Sharon Johnson Coleman; Filed Nov. 11, 2016.
*Medline Industries Inc.* vs *C.R. Bard, Inc.*; to C.R. Bard's LPR 2.3 Contentions. Civil Action No. 1:17-cv-7216; Judge Sara L. Ellis; Filed Jan. 16, 2018.
*Medline Industries Inc.* vs *C.R. Bard, Inc.*; Declaration of Dylan J Raife in Support of Bard Opening Claim Construction Brief; Civil Action No. 1:16-cv-03529; Judge Sharon Johnson Coleman; Filed Nov. 11, 2016.
*Medline Industries Inc.* vs *C.R. Bard, Inc.*; Exhibit 11 to Declaration of Richard Meyst Regarding Claim Construction; Civil Action No. 1:14-cv-03618; Judge John Z Lee; Filed Jul. 8, 2016.
*Medline Industries Inc.* vs *C.R. Bard, Inc.*; Declaration of Kevin A. Lake in Support of Medline Response to Bard Claim Construction Brief: Civil Action No. 1:14-cv-03618; Judge John Z. Lee; Filed Jul. 8, 2016.
*Medline Industries Inc.* vs *C.R. Bard. Inc.*; Exhibit G to Declaration of Dylan J. Raife in Support of Bard Opening Claim Construction Brief; Civil Action No. 1:16-cv-03529; Judge Sharon Johnson Coleman; Filed Nov. 11, 2016.
Inter Partes Review—Patent Owner's Prelim. Response; U.S. Pat. No. 9,795,761; Inter Partes Review No. IPR2019-00109; Filed Feb. 22, 2019.
Inter Partes Review—Patent Owner's Prelim. Response; U.S. Pat. No. 9,808,400; Inter Partes Review No. IPR2019-00208; Filed Mar. 7, 2019.
IPR Petition 2001, Declaration of Meyst dated Jan. 11, 2019; IPR 2019-00035, IPR-2019-00036.
IPR Petition 2002, Declaration of Weintraub dated Jan. 11, 2019; IPR 2019-00035, IPR-2019-00036.
IPR Petition Exhibit 2001, Declaration of Meyst dated Feb. 22, 2019; IPR2019-00109.
IPR Petition Exhibit 2001, Declaration of Meyst dated Mar. 7, 2019; IPR2019-00208.
IPR Petition Exhibit 2001; Declaration of Meyst dated Mar. 7, 2019; IPR2019-00223.
IPR Petition Exhibit 2002, Declaration of Weintraub dated Mar. 7, 2019; IPR2019-00208.
IPR Petition Exhibit 2002, Declaration of Weintraub dated Mar. 7, 2019; IPR2019-00223.
*Medline Industries, Inc.* vs *C.R. Bard, Inc*; No. 1:17-cv-03618; Medline's Supplemental Responses to Bard's Interrogatory No. 1-24 (redacted), dated Apr. 20, 2016; Filed as IPR Peition Exhibit 2013 in IPR2019-00035 and IPR2019-00036.
*Medline Industries, Inc.* vs *C.R. Bard, Inc*; No. 1:17-cv-3539; Medline's Second Supplemental Responses to Bard's Interrogatory No. 11, 14, and 15 (redacted), dated Oct. 26, 2017; Filed as IPR Peition Exhibit 2014 in IPR2019-00035 and IPR2019-00036.
*Medline Industries, Inc.* vs *C.R. Bard, Inc*; No. 1:17-cv-7216; Medline's Objection and Response to Bard's First Set of Interrogatories (redacted), dated Oct. 1, 2018; Filed as IPR Peition Exhibit 2012 in IPR2019-00035 and IPR2019-00036.
Inter Partes Review—Patent Owner's Prelim. Response; U.S. Pat. No. 9,808,596; Inter Partes Review No. IPR2019-00223; Filed Mar. 7, 2019.
Webster's Dictionary Definition of "Intend"; Webster's Third New International Dictionary of the English Language unabridged (1961); filed as IPR Petition Exhibit 2016 in IPR 2019-00035.
"Decision Instituting Inter Partes Review", IPR2019-00035; U.S. Pat. No. 9,745,088; Mailed Apr. 10, 2019.
"Decision Instituting Inter Partes Review", IPR2019-00036; U.S. Pat. No. 9,745,088; Mailed Apr. 10, 2019.
"Inter Partes Review—Patent Owner's Prelim Response", U.S. Pat. No. 9,745,088; Inter Partes Review No. IPR2019-00035; Filed Jan. 11, 2019.
"Inter Partes Review—Patent Owner's Prlim Response", U.S. Pat. No. 9,745,088; Inter Partes Review No. IPR2019-00036; Filed Jan. 11, 2019.
"Inter Partes Review No. IPR2019-00109", Petition for Review; U.S. Pat. No. 9,795,761; Filed Oct. 24, 2018.
"IPR 2019-00109", Exhibit 1031—Declaration of Jennifer Tomes filed in U.S. Appl. No. 12/647,515 dated Dec. 7, 2012.
"IPR 2019-00109", U.S. Pat. No. 9,795,761; Filed Oct. 24, 2018; Declaration of Dr. Edward Yun.
"IPR Decision Instituting Inter Partes Review", IPR2019-00109; U.S. Pat. No. 9,795,761; Mailed May 6, 2019.
"IPR Exhibit 1022", Email from Medline counsel re claims constructions; IPR2019-0035; Filed Oct. 4, 2018.
"IPR Petition Exhibit 1024", Email from Bard counsel re claims constructions; IPR2019-0035; Filed Oct. 4, 2018.
"IPR2019-00109", Exhibit 1026—Bard's Opening Claim Construction Brief; Civil Action No. 1:17-cv-07216; Dated Oct. 10, 2018; Filed Oct. 24, 2018 as exhibit 1026.
"IPR2019-00109", Exhibit 1030—Medline Industries, Inc.'s Final Infringement Contentions; Filed Jul. 24, 2018 in Civil Action No. 1:17-cv-07216; Filed as exhibit Oct. 24, 2018.
"IPR2019-00109", U.S. Pat. No. 9,795,761; Filed Oct. 24, 2018; Exhibit 1002 Declaration of Michael Plishka.
"Markman Decision", *Medline Industries, Inc.* vs *C.R. Bard, Inc*; Case No. 1:16-cv-03529\; Memorandum Opinion and Order; Judge Sharon Johnson Coleman Issued Dec. 28, 2018.
"Markman Hearing", *Medline Industries, Inc.* vs *C.R. Bard, Inc*; Case No. 1:17-cv-07216; Memorandum Opinion and Order; Judge Sara L. Ellis; Issued Jan. 28, 2019.
"Petition for Inter Partes Review", IPR 2019-00208; U.S. Pat. No. 9,808,400; Filed Nov. 7, 2018.
"Petition for Inter Partes Review", IPR 2019-00223; U.S. Pat. No. 9,808,596; Filed Nov. 7, 2018.
Lawrence, Samantha Q., "Notice of Allowance", U.S. Appl. No. 29/479,600, filed Jan. 17, 2014; dated Apr. 25, 2019.
Mian, Ali, "Non-Final Office Action", Canadian Application No. 2,837,324; dated Oct. 3, 2018.
Poon, Robert, "Final Office Action", U.S. Appl. No. 15/703,514, filed Sep. 13, 2017; dated May 2, 2019.
Poon, Robert, "Non-Final Office Action", U.S. Appl. No. 15/803,393, filed Nov. 3, 2017; dated Oct. 15, 2018.
Poon, Robert, "Non-Final Office Action", U.S. Appl. No. 15/804,520, filed Nov. 6, 2017; dated Nov. 2, 2018.
Poon, Robert, "Notice of Allowance", U.S. Appl. No. 14/265,920, filed Apr. 30, 2014; dated Nov. 28, 2018.
Pothier, Andrew, "Office Action", Canadian Application No. 2,837,289; dated Oct. 29, 2018.
*Medline Industries, Inc.* vs *C.R. Bard, Inc*; No. 14-cv-3618; Memorandum in Support of C.R. Bard's Motion for Leave to File Second Amended Answer to Add Counterclaim; Filed Sep. 25, 2015.
*Medline Industries, Inc.* vs *C.R. Bard, Inc*; No. 1:14-cv-03618; Defendant C.R. Bards, Inc's Second Amended Answer to Second Amended Complaint; Filed Sep. 25, 2015.

(56) References Cited

OTHER PUBLICATIONS

*Medline Industries, Inc.* vs *C.R. Bard, Inc*; Exhbit J to Declaration of Nicole M. Smith; Civil Action No. 1:14-cv-03618; Judge John Z. Lee; Filed Jun. 4, 2016.
Marcetich, Adam, "Non-Final OA", U.S. Appl. No. 15/640,224, filed Jun. 30, 2017; Mailed Jul. 10, 2019.
Poon, Robert, "Final Office Action" U.S. Appl. No. 15/803,383, filed Nov. 3, 2017; dated Jul. 25, 2019.
Pothier, Andrew , "Non-Final Office Action", Canadian Application No. 2,837,289; dated Jun. 27, 2019.
Power, , "Postoperative behaviour changes and pain in children, 2 to 12 years, following inpatient and day case surgery", University College London; http://discovery.ucl.ac.uk/643438/1/643438.pdf, Aug. 2010.
Zeev, et al., "Family-centered Preparation for Surgery Improves Perioperative Outcomes in Children: A randomized Controlled Trial", Anesthesiology, 106, pp. 65-74; https://anesthesiology.pubs.asahq.org/article.aspx?articleid=1922803 ; Jan. 2007.
"Decision Instituting IPR", IPR 2019-00208; U.S. Pat. No. 9,808,400; Dated Jun. 6, 2019.
"Decision Instituting IPR", IPR 2019-00223; U.S. Pat. No. 9,808,596; Dated Jun. 6, 2019.
Pothier, Andrew , "Office Action", Canadian Application No. 2,822,905; dated Jun. 13, 2019.
"Expert Report of Barbara Weintraub", Civil Action No. 1:14-cv-03618; Confidential Information Redacted Pursuant to Court Order; Dated Jun. 14, 2019.
"Expert Report of Barbara Weintraub", Civil Action No. 1:16-cv-03529; Confidential Information Redacted Pursuant to Court Order; Dated Aug. 1, 2019.
"Expert Report of Dr. Edward Yun", Civil Action No. 1:14-cv-03618; Confidential Information Redacted Pursuant to Court Order; Dated Jun. 13, 2019.
"Expert Report of Dr. Edward Yun", Civil Action No. 16-cv-3529; Confidential Information Redacted Pursuant to Court Order; Dated Aug. 1, 2019.
"Expert Report of Dr. Edward Yun Related to Damanges, Non-Infringement, and New Evidence of Alleged Secondary Considerations", Civil Action No. 1:14-cv-03618; Confidential Information Redacted Pursuant to Court Order; Dated Jul. 23, 2019.
"Expert Report of Dr. John Abraham", Civil Action No. 1:14-cv-03618; Confidential Information Redacted Pursuant to Court Order; Dated Jun. 14, 2019.
"Expert Report of Dr. John Abraham", Civil Action No. 1:16-cv-03529; Confidential Information Redacted Pursuant to Court Order; Dated Aug. 1, 2019.
"Expert Report of Dr. Steven Brooks", Civil Action No. 14-cv-3618; Confidential Information Redacted Pursuant to Court Order; Dated Jul. 25, 2019.
"Expert Report of Karl R Leingsing, MSME, PE Regarding Alleged Evidence of Secondary Considerations", Civil Action No. 1:14-cv-3618; Confidential Information Redacted Pursuant to Court Order; Dated Jun. 14, 2019.
"Expert Validity Report of Dr. John Abraham", Civil Action No. 1:14-cv-03618; Confidential Information Redacted Pursuant to Court Order; Dated Jul. 25, 2019.
"Opening Expert Report of Karl R Leinsing, MSME, PE", Civil Action No. 1:14-cv-3618; Confidential Information Redacted Pursuant to Court Order; Dated Jun. 14, 2019.
"Opening Expert Report of Karl R. Leinsing, MSME, PE", Civil Action No. 1:16-cv-3529; Confidential Information Redacted Pursuant to Court Order; Dated Aug. 1, 2019.
"Rebuttal Expert Report of Barbara Weintraub", Civil Action No. 1:14-cv-03618; Confidential Information Redacted Pursuant to Court Order; Dated Jul. 25, 2019.
"Rebuttal Expert Report of Richard Hillstead, Ph.D.", Civil Action No. 1:14-cv-3618; Confidential Information Redacted Pursuant to Court Order; Dated Jun. 14, 2019.
Poon, Robert, "Final Office Action", U.S. Appl. No. 15/804,520, filed Nov. 6, 2017; dated Aug. 8, 2019.
Mian, Ali, "Office Action", Canadian Application No. 2,837,324; Reference No. 10055U CIP6 Ca; dated Sep. 3, 2019.
Poon, Robert, "NonFinal Office Action", U.S. Appl. No. 16/258,231, filed Jan. 25, 2019; dated Oct. 2, 2019.
Van Poelgeest, A, "Exam Report", EP Application No. 12792423.1; dated Sep. 17, 2019.
Van Poelgeest, A, "Examination Report", EP Application No. 11 854 003.8-1113; dated Sep. 17, 2019.

\* cited by examiner

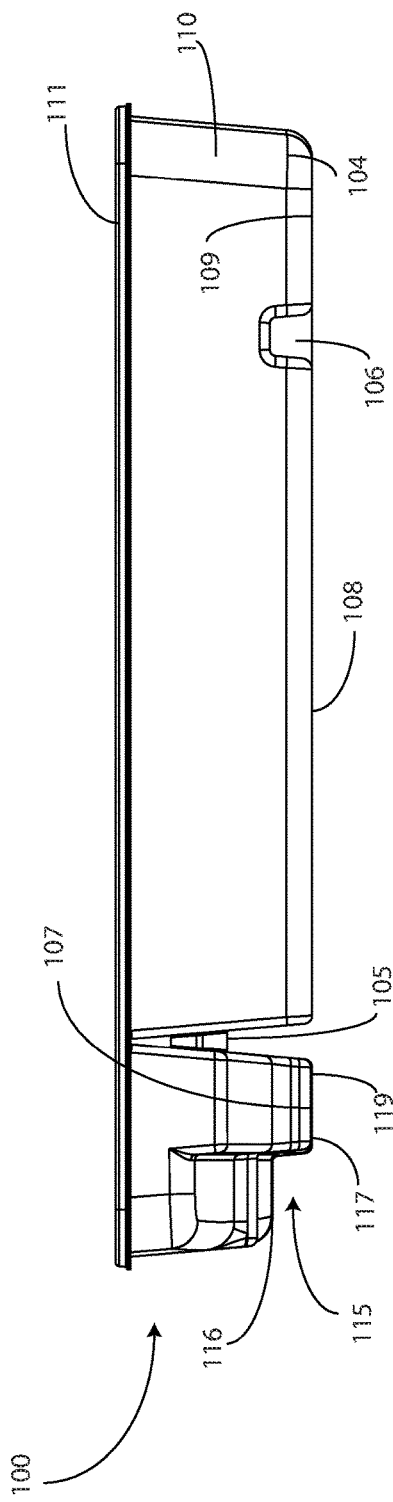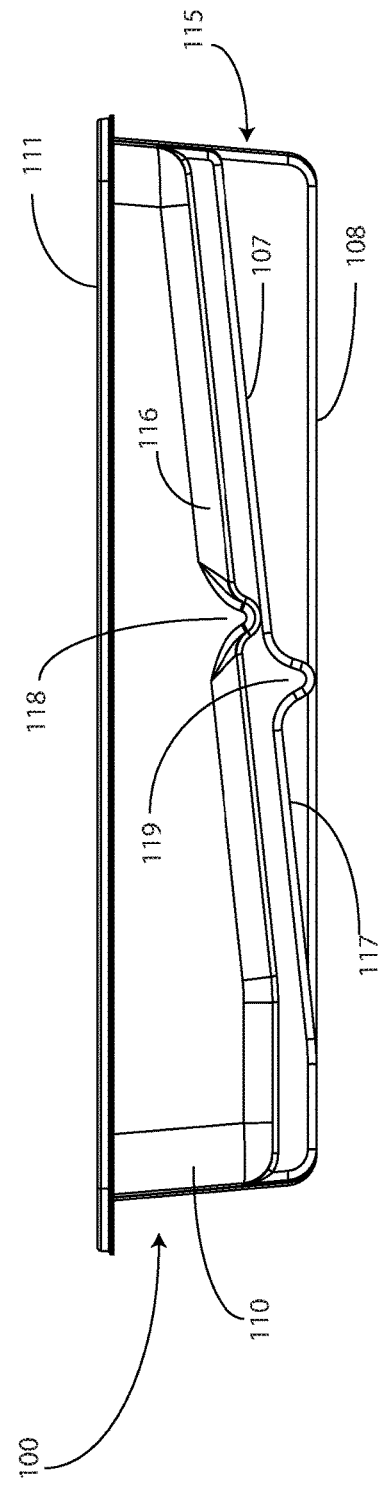

PATIENT EDUCATION: INFORMATION ABOUT CATHETERIZATION — 1206

4. What is a 'catheter-associated' urinary tract infection (UTI)?

Some helpful germs live in our urinary tract. But if a catheter introduces 'outside' germs, they can cause an infectio n. That's why hands must be washed before handling your catheter. It's also why catheters must be removed as soon as possible. — 1801

5. What are some symptoms if you have a urinary tract infection (UTI)?
- Sudden fever and/or bloody urine.
- Burning or painfulurination, or pain below the stomach.
- Frequent, or more urgent, urinating after catheter is removed.

Tell your physician/provider right away, because an antibiotic may be needed. — 1802

6. What about when you're going home?
- If you'll be using a catheter, make sure your health care provider fully explains how to care for it.
- Be sure to find out who to contact if you have questions after you get home.

— 1803

My physician's/provider's information: _____

Phone Number: _____

— 1804

Adapted from: Centers for Disease Control and Prevention. FAQs about "Catheter-Associated Urinary Tract Infection." Available at: http://www.cdc.gov/ncidod/dhqp/pdf/guidelines/CA-UTI_tagged.pdf. Accessed March 25, 2009.

©2009 Medline Industries, Inc., Silvertouch and Aloetouch are trademarks of Medline Industries, Inc. Assembled in USA by Medline Industries, Inc., Mundelein, IL. 60060-4486 USA. Distributed in Canada by Medline Canada Corp., Oakville, Ontario L2L6R2". www.medline.com 1-800-MEDLINE DYND160416 RG09/DYN 80759U

*FIG. 18*

CATHETER TRAY, PACKAGING SYSTEM, AND ASSOCIATED METHODS

CROSS REFERENCE TO PRIOR APPLICATIONS

This application is a continuation of, and therefore claims priority under 35 U.S.C. § 120 from, U.S. patent application Ser. No. 12/647,515, filed Dec. 27, 2009, which claims priority and benefit under 35 U.S.C. § 119 from Provisional Application 61/183,629, filed Jun. 3, 2009, and which is also a continuation-in-part of, and therefore claims priority under 35 U.S.C. § 120 to, U.S. patent application Ser. No. 12/495,148, filed Jun. 30, 2009, which claims priority under 35 U.S.C. § 119(e) from Provisional Application 61/183,629, filed Jun. 3, 2009, each of which is incorporated herein by reference.

BACKGROUND

Technical Field

This invention relates generally to storage containers for medical devices, and more particularly to a storage container for a long, flexible medical implement, such as a catheter, and related medical devices, as well as an instruction manual included therewith.

Background Art

Medical devices, including surgical instruments, supplies, and so forth, are generally shipped from manufacturer to medical services provider in sterile packaging. For example, a scalpel may be shipped to a surgeon in a plastic, vacuum-sealed, sterile package. Similarly, bandages may be shipped in paper, plastic, or paper composite sterile wrappers. When the medical services provider is ready to use the medical supply, the sterile package is removed. The medical services provider then uses the object in accordance with the procedure being performed.

While conventional packaging works well for objects having a generally unchanging form factor, special considerations have to be taken into consideration for some medical supplies. By way of example, catheter assemblies and other flexible equipment is generally shipped in a coiled configuration. Once the sterile packaging is removed, the catheter must be uncoiled prior to use. Care must be taken in shipping, unwrapping, and using the catheter. For instance, if a catheter is inadvertently bent, kinked, or otherwise damaged, it may no longer be suitable for use. Compounding this issue, catheters are available in a variety of lengths ranging from 100 centimeters to over 250 centimeters.

Traditional catheters are packaged, for example, in individual packaging. The catheter and card are then sealed in a sterile plastic wrap. These catheters are prone to damage in shipment, storage, and when being unpacked, as the card and wrap provide little physical protection.

Some manufacturers have started shipping catheters and other similar devices in flat plastic trays. For example, U.S. Pat. No. 6,068,121 to McGlinch teaches one such tray. The tray has several specifically contoured loops such that one universal tray will accommodate several different sized catheters. Such packaging presents a problem, however, in that large amounts of storage space are taken with a universal tray, especially when a relatively short catheter is shipped therein. Additionally, when in use, these trays occupy large amounts of a medical service provider's sterile workspace or table, leaving little room for related components, such as lubricants, fluid bags, and so forth.

There is thus a need for an improved container for flexible medical devices or catheters that facilitates more effective and simpler deployment of the device during a procedure.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 4 illustrates a front elevation view of one embodiment of a tray for a catheter or similar assembly in accordance with embodiments of the invention.

FIG. 5 illustrates a cut-away, left elevation view of one embodiment of a tray for a catheter or similar assembly in accordance with embodiments of the invention.

FIGS. 14-19 illustrate exemplary panels of printed instructions in accordance with embodiments of the invention.

Figure 1:
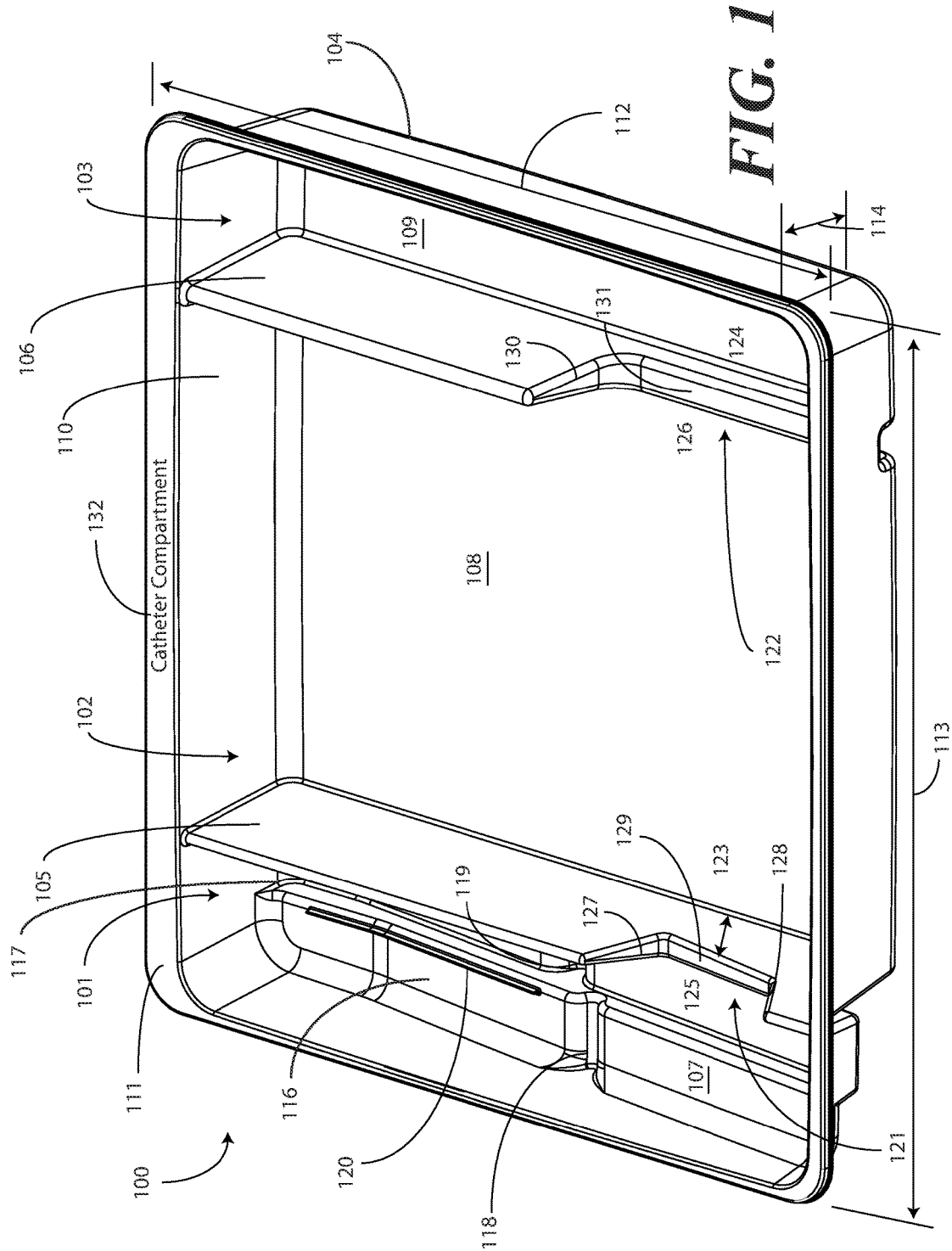
FIG. 1 illustrates a top, front, right perspective view of one embodiment of a tray for a catheter or similar assembly in accordance with embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide a tray configured to accommodate a coiled medical device such as a catheter or catheter assembly. In addition to accommodating the coiled medical device, embodiments of the present invention are also configured to contain devices and materials intended for use with the coiled medical device.

Using a catheter assembly as an example, when a catheter assembly is inserted into a patient, sterile water may be used to inflate the catheter. Additionally, the catheter may be coated in a lubricating jelly prior to insertion into the patient. Fluids and other samples may then be monitored and obtained from the patient via the catheter. Embodiments of the present invention provide a single container configured to accommodate not only the catheter assembly and fluid bag, but also syringes containing sterile water or lubricants. Further, the tray can accommodate a sterile specimen jar for capturing samples taken from the patient via the catheter.

In addition to simply accommodating these corresponding medical devices, in one embodiment the tray is configured to provide the medical services provider with mnemonic devices instructing them in which order to use each device. For example, a compartment containing syringes, in one embodiment, includes an inclined, stair-stepped bottom member to present the plungers of each syringe at an easy to reach angle and at different heights based upon order of use.

Another advantage of embodiments of the present invention is that compartments have multi-purpose functionality. For example, in one embodiment, a container configured to accommodate a syringe having lubricating jelly disposed therein is also configured to be used as a lubricating jelly applicator. A medical services provider first dispenses the lubricating jelly into the syringe compartment. The medical services provider then passes the catheter from another compartment through an opening in a barrier separating the compartments into the lubricating jelly. As such, the tray not only serves as a shipping and storage container for an assembly of devices used with a catheter procedure, but also as an application device to assist a medical services provider in using those products together.

Figure 2:
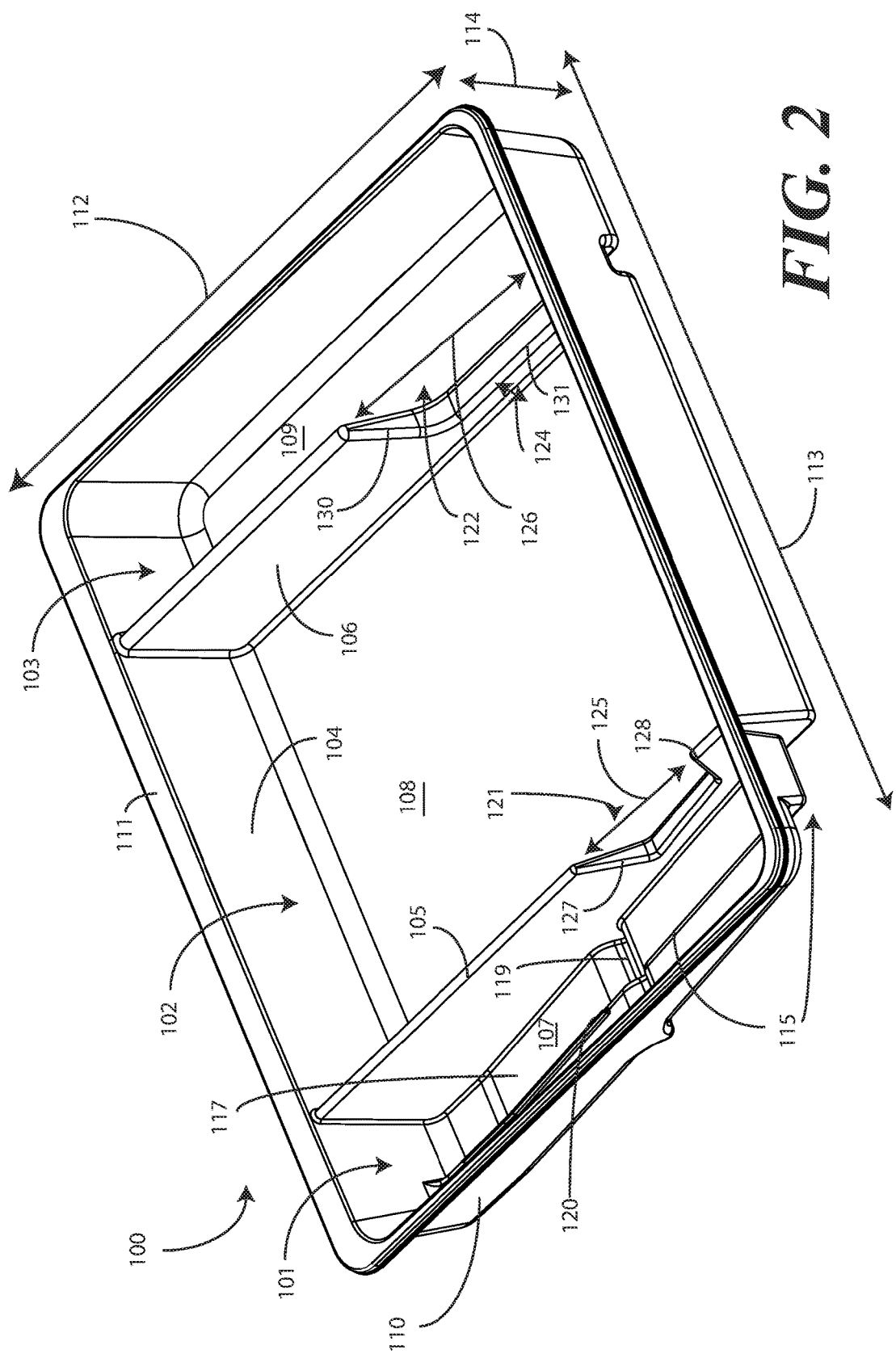
FIG. 2 illustrates a top, front, left perspective view of one embodiment of a tray for a catheter or similar assembly in accordance with embodiments of the invention.
Figure 3:
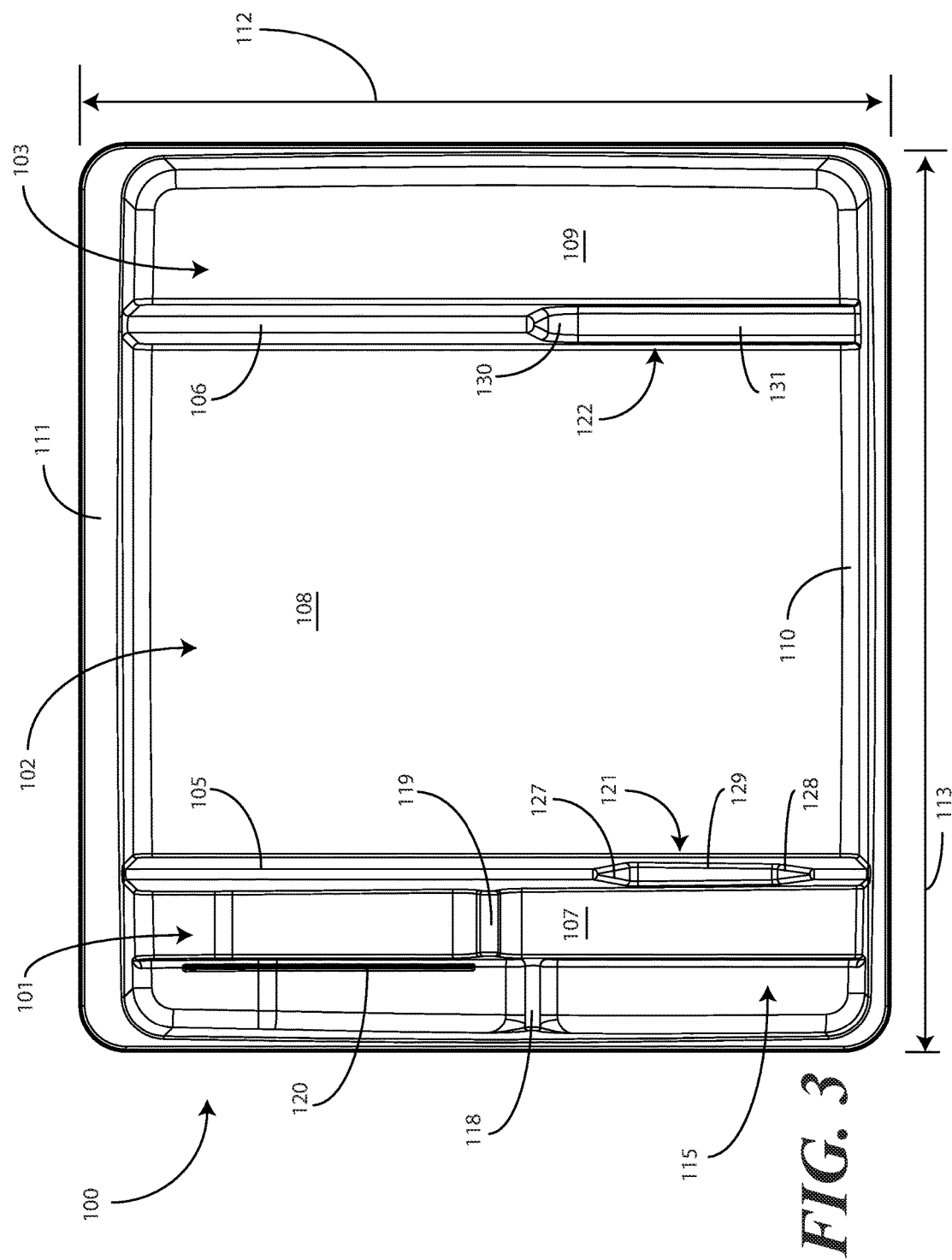
FIG. 3 illustrates a top plan view of one embodiment of a tray for a catheter or similar assembly in accordance with embodiments of the invention.
Figure 6:
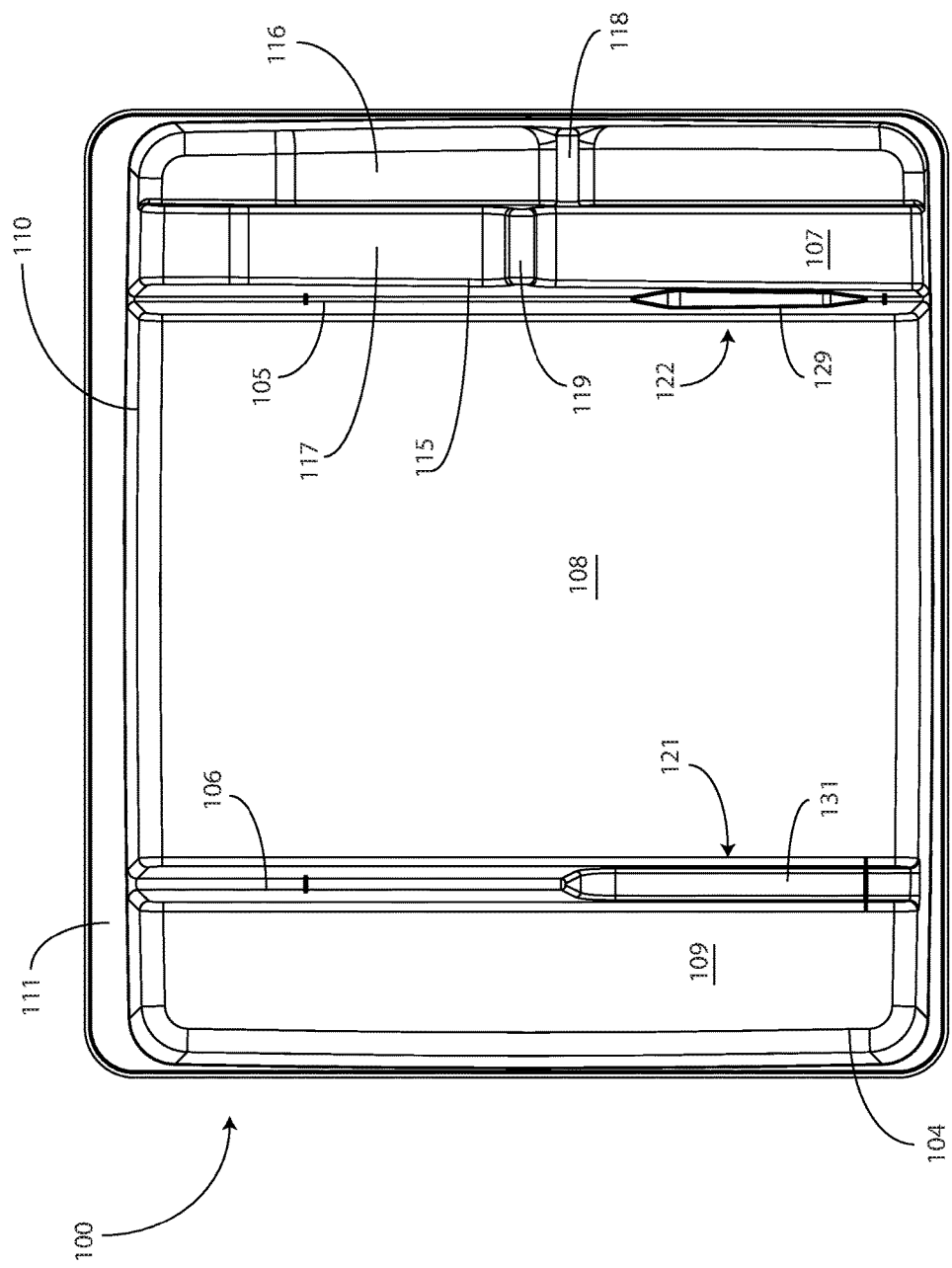
FIG. 6 illustrates a bottom plan view of one embodiment of a tray for a catheter or similar assembly in accordance with embodiments of the invention.

Turning now to FIGS. 1-6, illustrated therein are views of one embodiment of a tray 100 configured to accommodate a catheter assembly in accordance with embodiments of the invention. FIG. 1 illustrates a top, front right perspective view of the tray 100. FIG. 2 illustrates a top, front, left perspective view of the tray 100. FIG. 3 illustrates a top plan view of the tray 100. FIG. 4 illustrates a front elevation view of the tray 100. FIG. 5 illustrates a cut-away, left elevation view of one embodiment of a tray 100. Likewise, FIG. 6 illustrates a bottom plan view of the tray 100. For simplicity of discussion, these figures will be referred to collectively with like reference numerals referring to identical or functionally similar elements throughout the separate views.

The tray 100, in one embodiment, is formed by a contoured surface 104 that defines the various features and compartments of the tray 100. The contoured surface 104 of the tray 100 can be manufactured in various ways. For example, in one embodiment, the tray 100 can be thermally formed on a mold from a soft thermoplastic, such as styrene or polystyrene. In another embodiment, the tray 100 can be injection molded. In another embodiment, the tray can be poured on a mold using a quick setting plastic, epoxy, or resin. Other methods of manufacture will be obvious to those of ordinary skill in the art having the benefit of this disclosure.

Exemplary dimensions for one embodiment of the tray 100 are as follows: The length 112 can be between nine and twelve inches, such as ten inches. One illustrative length 112 may be 10.380 inches. Similarly, the width 113 can be between eight and eleven inches, such as nine inches. One illustrative width 113 is 9.250 inches. The height 114 can be between one and three inches. One illustrative height 114 is 1.750 inches.

In one embodiment, the tray 100 includes three main compartments: a first compartment 101, a second compartment 102, and a third compartment 103. The first compartment 101 is separated from the second compartment 102 by a first barrier 105. The second compartment 102 is separated from the third compartment 103 by a second barrier 106.

In one embodiment, the compartments are open from the top of the tray 100—the top being opposite the base members of the tray 100—and are bounded on the bottom by a first base member 107, a second base member 108, and a third base member 109. The compartments are bounded on the sides by a perimeter wall 110. In the illustrative "open top" embodiment of FIG. 1, the perimeter wall 110 ends in a horizontal flange 111 extending substantially orthogonally from the perimeter wall 110. It will be clear to those of ordinary skill in the art having the benefit of this disclosure that embodiments other than that shown in FIG. 1 are possible without departing from the spirit and scope of the invention. For instance, the top of the tray 100 could have a hinged or snap-coupled lid that is opened or removed to reveal the compartments there beneath.

In one illustrative embodiment, the tray 100 is configured to hold or otherwise accommodate all of the necessary devices and materials to perform a catheter-based procedure on a patient. Said differently, the tray 100 is configured to hold not only the catheter assembly, but the medical devices corresponding to catheter use as well. Using one illustrative procedure as an example, the following devices will be used: a syringe holding sterile water, a syringe holding lubricating jelly or another equivalent lubricant, a catheter assembly, skin cleansing or preparation materials, and a specimen jar. The various compartments and features of the tray 100 shown in FIGS. 1-6 will be described for use with these devices. As will be described in more detail below, additional objects can be included with the tray, such as one or more towels, a drape to cover the patient, rubber gloves, hand sanitizing materials, swab sticks, a securement device, a Foley insert tag, a printed instruction pamphlet, and so forth. The syringe holding sterile water, syringe holding lubricating jelly, catheter assembly, and specimen jar are used for illustration purposes only, as it will be clear that other objects may be added to or substituted for these objects. Further, subsets of these objects may be used.

In one embodiment suitable for procedures using the syringe holding sterile water, syringe holding lubricating jelly, catheter assembly, and specimen jar, in one embodiment, the tray 100 is configured such that these objects are ordered in accordance with their use during the procedure. For example, in one embodiment the tray 100 includes a first compartment 101 for accommodating one or more syringes, a second compartment 102 for accommodating the catheter assembly, and a third compartment 103 for accommodating the specimen jar. These devices stowed in the various compartments will be illustrated and described with respect to FIGS. 7-10 below. The discussion of FIGS. 1-6 will include the features of the tray 100 that make the tray 100 suitable for accommodating these devices.

For example, in one embodiment the first compartment base member 107 includes a stair-stepped contour 115 suitable for accommodating a plurality of syringes at different heights. For example, a first step portion 116 of the stair-stepped contour 115 may be at a different height within the tray 100 than a second step portion 117 of the stair-stepped contour. In the illustrative embodiment of FIGS. 1-6, the first step portion 116—which is disposed farther from the first barrier 105 than the second step portion 117—is shallower than the second step portion 117. Said differently, the second step portion 117 is disposed at a greater depth within the tray 100 than the first step portion 116.

The stair-stepped contour 115 can be used as mnemonic device when multiple syringes are stored within the first compartment 101. For example, it may be intuitive that a syringe placed on a higher step portion may need to be used first. This intuition is further enforced when the higher step portion is disposed farther to the left in a left-to-right usage configuration. Thus, a user receives a mnemonic reminder to use a syringe disposed on the first step portion 116 prior to a syringe disposed on the second step portion 117, as it is both higher and farther to the left.

Where syringes are stowed in the first compartment 101, the first compartment base member 107 can further be configured for syringe ease of use. For example, in one embodiment the first compartment base member 107 is inclined relative to other compartment base members. In the illustrative embodiment of FIGS. 1-6, the second compartment base member 108 and third compartment base member 109 are substantially coplanar with each other. Further, the second compartment base member 108 and third compartment base member 109 are generally flat in these views, although it will be clear to those of ordinary skill in the art having the benefit of this disclosure that contours could be incorporated into one or both of these base members.

In this illustrative embodiment, however, the first compartment base member 107 is configured to be inclined relative to one or both of the second compartment base member 108 and third compartment base member 109. As such, the stair-stepped contour 115 forms a ramp upon which syringes may be placed so that the plunger of each syringe is predisposed to project upward and out of the tray 100. Said differently, the stair-stepped contour 115 is configured such that the first step portion 116 and the second step portion 117 are disposed in a non-parallel orientation relative to the second compartment base member 108. This configuration makes it easier for a medical services provider to grasp the syringes and remove them from the tray 100.

The first compartment base member 107 may include other features suitable for accommodating one or more syringes as well. In one embodiment, one or both of the first step portion 116 and second step portion 117 include recesses 118,119 for accommodating a syringe flange. These recesses 118,119 generally function to prevent the syringes from sliding lengthwise within the first compartment 101. Similarly, in one embodiment one or both of the first step portion 116 and the second step portion 117 include protrusions 120 that help to prevent the syringes from sliding laterally within the first compartment 101.

In one embodiment, one or both of the first barrier 105 and the second barrier 106 include openings disposed therein. In the illustrative embodiment shown in FIGS. 1-6, the first barrier 105 includes a first opening 121 between the first compartment 101 and the second compartment 102. Similarly, the second barrier 106 includes a second opening 122 between the second compartment 102 and the third compartment 103. Each of these openings has an opening depth associated therewith. Similarly, each opening has an opening width associated therewith. In the illustrative embodiment of FIGS. 1-6, the first opening 121 is bounded by a first opening base member 129 and two inclined first opening side members 127,128, while the second opening 122 is bounded by a second opening base member 131, an inclined second opening side member 130, and the perimeter wall 110.

While the opening depths can be the same, in one embodiment the opening depths are different. For example, in the illustrative embodiments of FIGS. 1-6, the first opening 121 has a first opening depth 123 that is less than the second opening depth 124 of the second opening 122. Similarly, in one embodiment the opening widths are different. For example, in the illustrative embodiments of FIGS. 1-6, the first opening 121 has a first opening width 125 that is less than the second opening width 126 of the second opening 122. Such a disparity in opening depths and widths, as well as the inclusion of inclined opening side members, provides an advantage in some applications.

For instance, in many catheter procedures a pair of syringes—such as syringes having a one-half inch diameter—fits easily into the first compartment 101 when the tray 100 is made with the illustrative dimensions set forth above. However, some procedures require one or more of the syringes to be larger. For example, some syringes are larger in diameter. These larger syringes are capable of nesting within the first opening 121 and second opening 122. The inclined opening side members prevent the syringe from moving lengthwise, while the disparate opening heights present the plunger of the syringe to the medical services provider for easy removal from the tray 100.

The stair-stepped contour 115, working in tandem with the first opening 121, gives the tray additional advantages over prior art catheter containers. For instance, when the first compartment 101 has a first compartment base member 107 configured with a stair-stepped contour 115, the first compartment 101 can be used as a lubricant applicator for the catheter.

Specifically, the medical services provider may dispense the lubricating jelly along the second step portion 117. As the second step portion 117 is lower in the tray 100 than the first step portion 116, the second step portion 117 serves as a channel in which the lubricating jelly may spread. A medical services provider may then pass the catheter through the first opening 121, through the channel formed by the second step portion 117, i.e., along the second step portion 117 through the dispensed lubricating jelly, and out the top of the tray 100 to the patient. This feature of the tray 100 greatly eases the application of lubricating jelly to the catheter when compared to prior art solutions. In one embodiment, the tray 100 is packaged with printed instructions showing the medical services provider how to apply lubricating jelly in this manner. The printed instructions will be described in more detail below with respect to FIGS. 12-23.

This particular feature highlights another advantage of the "compartmentalized" structure of various embodiments of the invention. As the tray 100 includes multiple compartments, various tasks associated with a catheterization procedure can be completed while keeping the catheter within the tray 100. The ability to keep the catheter in the tray 100 reduces the risk that the catheter or corresponding devices will be contaminated with bacteria or microbes on other objects within the procedure room. For example, when the first compartment 101 is used to apply lubricating jelly to the catheter, the lubricating jelly can be applied while the catheter is contained within the tray 100, thereby reducing the risk that the catheter will become contaminated. This correspondingly reduces the risk of infection for the patient receiving the catheter.

Prior art systems, for example such as those in which the catheterization procedure components are shipped in separate containers, may contribute to substandard techniques in that the catheter can become contaminated when moving it from its shipping container. Consequently, the patient can be at an elevated risk of infection as the catheter is moved from one tray to another. Embodiments of the present invention solve this problem by providing a single level tray 100 with compartments. Further, in one embodiment the first compartment 101 includes the first opening 121 so the catheter can stay in place during and after lubrication. By having easy access to the components disposed in the single level tray 100, the medical services provider can more easily prepare and use the components within the tray 100. This helps to minimize the risk of contaminating the patient or the sterile field during the procedure.

In one embodiment, the second step portion 117 is configured to be inclined at a shallower angle than the first step portion 116 in at least a portion opposite the recess 119 from the first opening 121. When configured in such a fashion, the second step portion 117 includes a "cutdown" so that the catheter can stay within the channel both during and after lubrication.

Additionally, the catheter can be placed in both the first opening 121 and second opening 122 during lubrication. When positioned in this configuration, the second opening 122 helps to align the catheter with the first opening for easy passage through the lubrication channel formed by the second step portion 117.

The tray 100 of FIGS. 1-6 includes additional advantages over prior art catheter packaging as well. For example, in one embodiment, instructions 132 or other graphical indicia can be printed, placed upon, or molded into the horizontal flange 111. In one embodiment, compartment designations can be placed above each compartment to ensure the medical services provider uses the correct device or material at the correct time. In another embodiment, expiratory dates for materials or devices disposed within the tray 100 may be placed on the horizontal flange 111. It will be obvious to those of ordinary skill in the art having the benefit of this disclosure that the invention is not so limited. Any number of various text or picture combinations can be printed on, placed upon, or molded into various parts of the tray. For instance, graphical indicia can be applied to the compartment base members in addition to the horizontal flange 111. Note that the horizontal flanges, in one embodiment, can terminate in downwardly protruding vertical flanges for increased stability during the printing process.

Another advantage of the tray 100 is that its compartmentalized configuration helps to reduce the risk of contaminating a patient or compromising the sterile nature of the components stored in the tray 100. Since both the catheter assembly and medical devices corresponding to catheter use are stored within the same tray 100, the risk of cross-contamination between sterile work areas and non-sterile spaces is minimized. Further, by having the catheter assembly and the devices corresponding to catheter use stowed in a one-level tray rather than a multi-level, stacked configuration, the medical services provider can more easily prepare and use the catheter and corresponding devices disposed within the tray 100.

Figure 7:
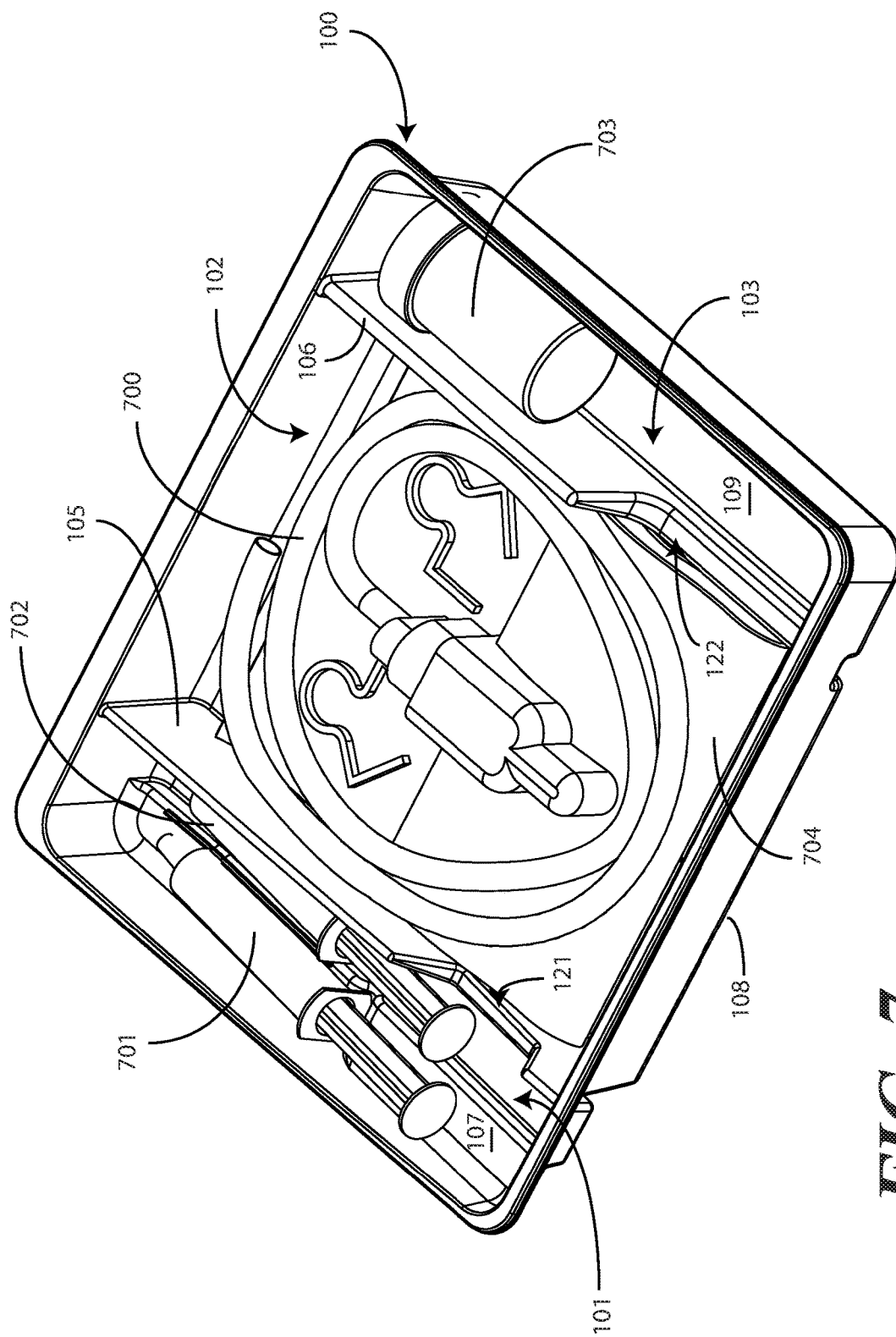
FIG. 7 illustrates a top, front, right perspective view of one embodiment of a tray for a catheter or similar assembly, with a catheter and corresponding procedural devices disposed therein, in accordance with embodiments of the invention.
Figure 8:
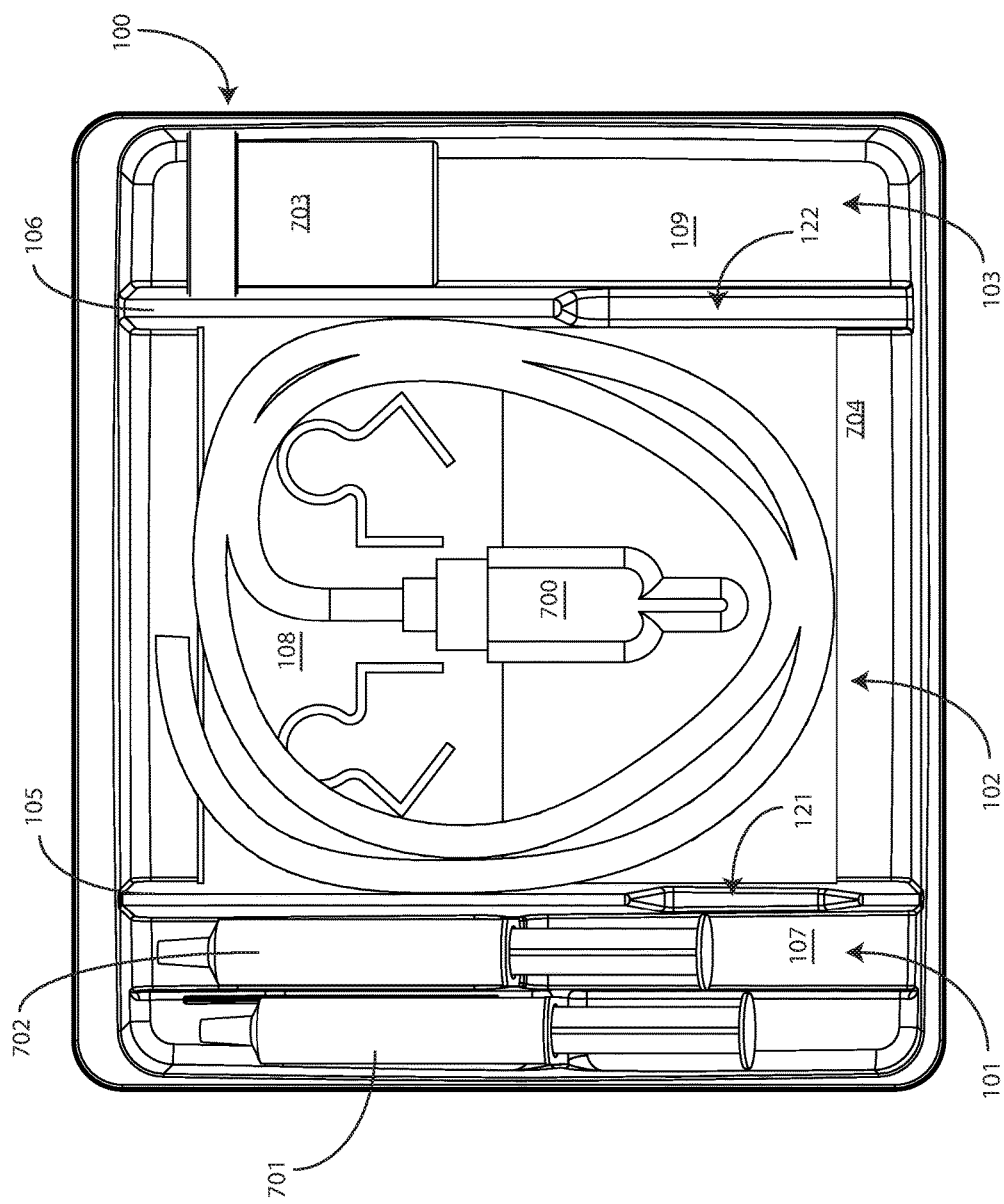
FIG. 8 illustrates a top plan view of one embodiment of a tray for a catheter or similar assembly, with a catheter and corresponding procedural devices disposed therein, in accordance with embodiments of the invention.
Figure 9:
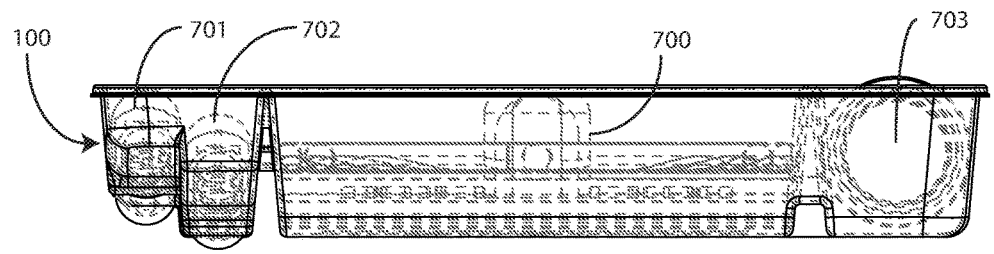
FIG. 9 illustrates a transparent, front elevation view of one embodiment of a tray for a catheter or similar assembly, with a catheter and corresponding procedural devices disposed therein, in accordance with embodiments of the invention.

Turning now to FIGS. 7-9, illustrated therein is a tray having a catheter assembly 700, syringes 701,702, and a specimen container 703 stored therein as a catheter packaging system in accordance with one embodiment of the invention. As with FIGS. 1-6, FIGS. 7-9 will be referred to collectively with like reference numerals referring to identical or functionally similar elements throughout the separate views. FIG. 7 illustrates a top, front, right perspective view of the catheter packaging system, while FIG. 8 illustrates a top plan view of the catheter packaging system. FIG. 9 illustrates a transparent, front elevation view of the catheter packaging system.

The illustrative catheter packaging system of FIGS. 7-9 includes a tray 100 having a first compartment 101, a second compartment 102, and a third compartment 103. In this illustrative embodiment, the first compartment 101 is configured to accommodate syringes 701,702. The second compartment 102 is configured to accommodate a coiled medical device, such as catheter assembly 700. The third compartment 103 is configured to accommodate the specimen container 703. The third compartment 103 can accommodate other materials as well, including skin sanitizers and cleansing liquids, solutions, or gels. As mentioned above, additional devices corresponding to catheter use, including towels, drapes, rubber gloves, and so forth, can be disposed in the tray 100 as well. As an illustration of this flexibility, a towel 704 is disposed beneath the catheter assembly 700.

As illustrated in FIGS. 1-6, each compartment of the tray 100 includes a compartment base member. Further, each compartment is separated by a barrier having an opening therein. A first barrier 105 having a first opening 121 therein separates the first compartment 101 from the second compartment 102. Similarly, a second barrier 106 having a second opening 122 therein separates the second compartment 102 from the third compartment.

Syringes 701,702 are disposed in the first compartment, with one syringe 701 being supported at a different elevation within the tray than the other syringe 702. The different elevations can be relative to each syringe 701,702, or to other components of the tray 100, such as the second compartment base member 108. Said differently, one syringe 701 is supported by the first compartment base member 107 at a shallower depth within the tray 100 than the depth of the second compartment base member 108. Further, where the first compartment base member 107 is inclined relative to other base members, one or both syringes 701,702 will be supported in a non-parallel configuration relative to the second compartment base member 108. This is most readily seen in FIG. 9.

As noted above, some medical procedures will call for more materials than can be accommodated by a syringe capable of fitting within the first compartment 101. For such procedures, the tray 100 can be packed with larger syringes. A large syringe (not shown) can be supported laterally within the tray 100 when it is placed across the tray 100 such that it lies within both the first opening 121 of the first barrier 105 and the second opening 122 of the second barrier 106. Such a syringe will pass across the top of the catheter assembly 700, but will be held in place by the side members of each opening.

Figure 10:
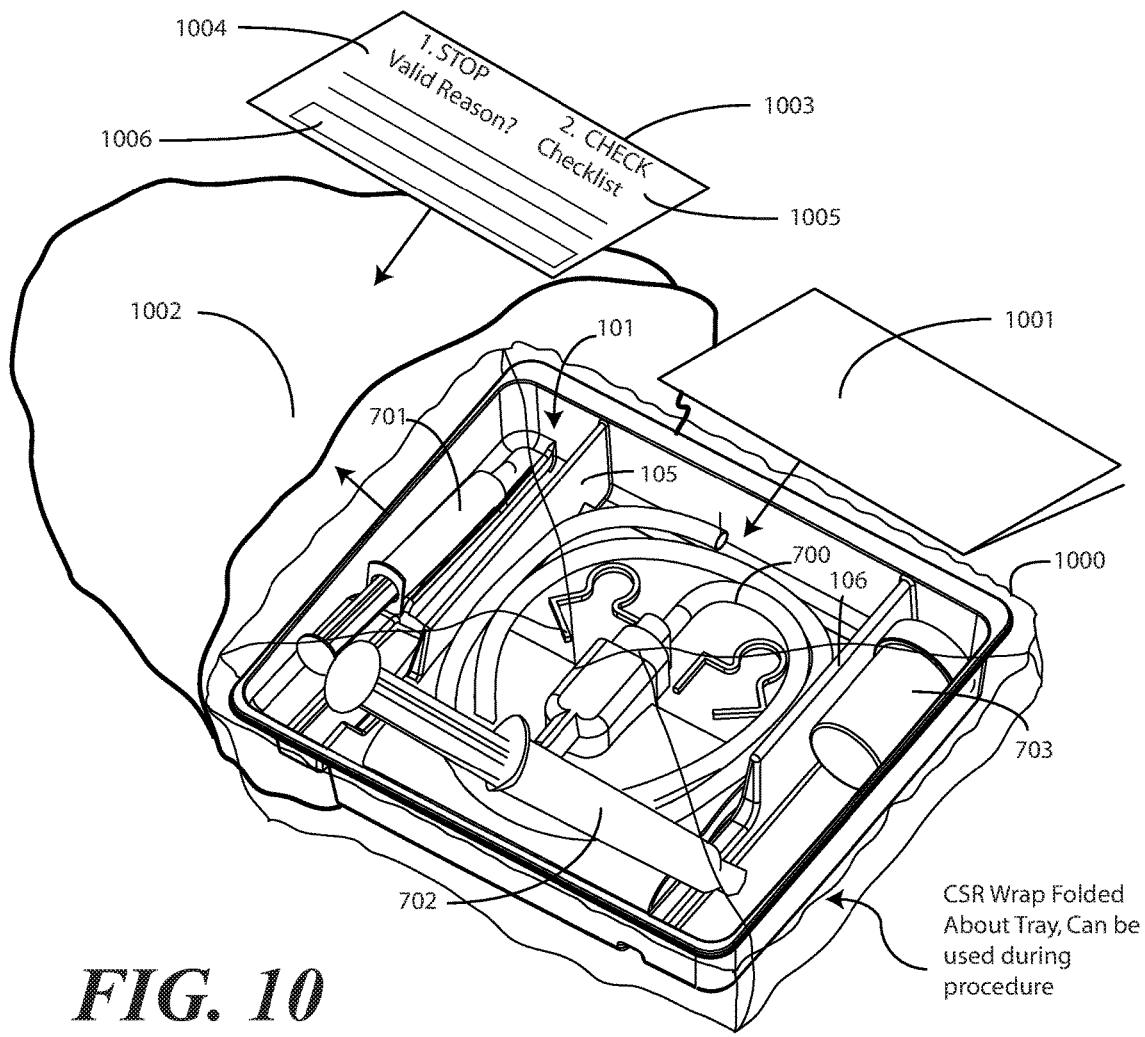
FIG. 10 illustrates a perspective view of one embodiment of a tray for a catheter or similar assembly, with a catheter and corresponding procedural devices disposed therein, along with instructions and packaging, in accordance with embodiments of the invention.

Turning now to FIG. 10, illustrated therein is an exploded view of the tray 100 having the catheter assembly 700, a pair of syringes 701,702, and a specimen container 703 disposed therein. While only a specimen container 703 is shown as being disposed in the third compartment, note that additional items could also be included within the third compartment, including swab sticks. Other devices could also be inserted into the tray 100 in various compartments as well. For example, in one embodiment, a catheter securement device, and a Foley insertion tag can be inserted into the second compartment 102. Also, note that the pair of syringes 701,702 can be configured as shown in FIG. 10, or alternatively can be both inserted in the first compartment, as described above. In the configuration of FIG. 10, rather than having both syringes 701,702 disposed within the first compartment 101, one syringe 702 is disposed laterally in the first opening 121 and the second opening 122 of the first barrier 105 and second barrier 106, respectively. This configuration is illustrative only.

Once the necessary components are disposed within the tray 100, the tray can be sealed with a CSR wrap 1000 to keep the internal components sterile. In one embodiment, as indicated in FIG. 10, the CSR wrap 1000 is folded about the tray 100 for sealing, and can be correspondingly unfolded to reveal the tray 100. Once unfolded, the CSR wrap 1000 can then be used in the catheter insertion process. For example, an unfolded CSR wrap 1000 can be used to provide a sterile field in which the tray 100 sits for unloading and subsequent use.

Printed instructions 1001 can then be attached to, disposed upon, or disposed within the tray 100. In one embodiment, the printed instructions 1001 include a health care services portion and a patient portion, as will be shown in FIGS. 12-13 below. The health care services portion can include instructions telling the health care services provider, for example, how to set up a sterile or otherwise clean work environment, how to prepare the catheter assembly 700 disposed within the tray, how to use the other devices within the tray, how to insert the catheter, how to secure the drainage bag to the catheter, how to empty the drainage bag, how to obtain a urine sample, and so forth. The instructions can include pictures or illustrations showing visually how the various steps should be done as well.

The patient portion can include helpful suggestions or instructions for the patient. The patient portion can be detachably coupled to the health care services portion, such as by a perforated line that is easily torn to separate the patient portion from the health care services portion. Examples of suggestions or instructions that may be included in the patient portion include information on what a catheter is, what the patient should understand about the catheter, how to reduce the chance of getting an infection, information about infections commonly associated with catheters, symptoms of infections commonly associated with catheters, and suggestions for home use of the catheter assembly 700. In one embodiment, the health care services portion may include an instruction for the health care services provider to detach the patient portion from the health care services portion and instructions to discuss the patient portion with the patient.

The health care services portion can tell the medical services provider how to perform a standard catheterization procedure. For instance, in one embodiment, the tray 100 is equipped with an adhesive label that can be used to identify the patient or specimen in the specimen container 703. Further, a label can be included to mark or otherwise identify the material in the fluid bag attached to the catheter. Such labels can include pre-printed fields, such as date, time and name. Further the printed instructions 1001 can notify the medical services provider that the devices disposed within the tray 100 are ordered corresponding to use during the catheterization procedure.

In another embodiment, the printed instructions 1001 can inform the medical services provider of special instructions. For instance, in one embodiment the printed instructions 1001 can inform the medical services provider not to leave a catheter in a patient for more than forty-eight hours without a physician's approval. Where the printed instructions 1001 include such information, the labels included in the tray 100 may have pre-printed fields for the time of insertion that can be filled in by the medical services provider performing the catheterization procedure.

Once the printed instructions 1001 have been affixed to, or placed with, within, or atop the tray 100, the assembly can be sealed in a sterile wrap 1002 such as a thermally sealed bag. The thermally sealed bag can optionally include a preformed opening. For example, in one embodiment, the opening can include one or more tabs that a health care services provider is instructed to pull to open the bag. Inclusion of a sterile wrap 1002 not only keeps the contents within the bag sterile, but also allows the instructions to be included with the tray assembly, yet outside the CSR wrap 1000.

In one embodiment the printed instructions 1001 are disposed atop the CSR wrap 1000 such that the health care services portion of the printed instructions 1001 is disposed on the top of the printed instructions 1001, with the patient portion being disposed adjacent to the CSR wrap 1000, such as when the printed instructions 1001 are configured as an accordion-style folded instruction pamphlet. While the printed instructions 1001 of one embodiment are configured as a folded, printed, separate article disposed atop the CSR wrap 1000, it will be clear to those of ordinary skill in the art having the benefit of this disclosure that the invention is not so limited. For example, in one embodiment the sterile wrap 1002 can be optional. In one embodiment, rather than including separate printed instructions 1001, the instructions for use can be printed on the CSR wrap 1000 as well.

Additional instruction materials may be included with the completed assembly as well. For example, in one embodiment an adhesive instruction tag 1003 can be affixed to the sterile wrap 1002. For example, in one embodiment the instruction tag 1003 can include information regarding whether a catheter procedure is needed. Text 1004 such as "Is there a valid clinical reason?" may be included under an instruction to "Stop" that includes the following information:

Before inserting the foley catheter, at least one of the following conditions should exist:
Acute urinary retention or obstruction
Precise measurement of urinary output needed
Select surgical procedures
Open sacral or perineal wounds in incontinent patient
Prolonged immobilization
End of life care
Further, checklist text 1005 may be included, such as "Checklist for Foley Catheter Insertion" included under the word "Check" that includes the following information:
Check Each Box Upon Completion:
Obtain order from physician/provider
Document clinical reason for insertion
Explain procedure to patient
Use smallest catheter possible
Perform hand hygiene
Follow aseptic technique
Additional information may also be included, such as a fillable form 1006 that provides fields for the date and time of insertion of the catheter to be recorded, the name of the healt care services provider, and the signature of the health care services provider. The above text 1004 for the instruction tag 1003 is illustrative only, and may be customized as desired by the manufacturer.

Figure 11:
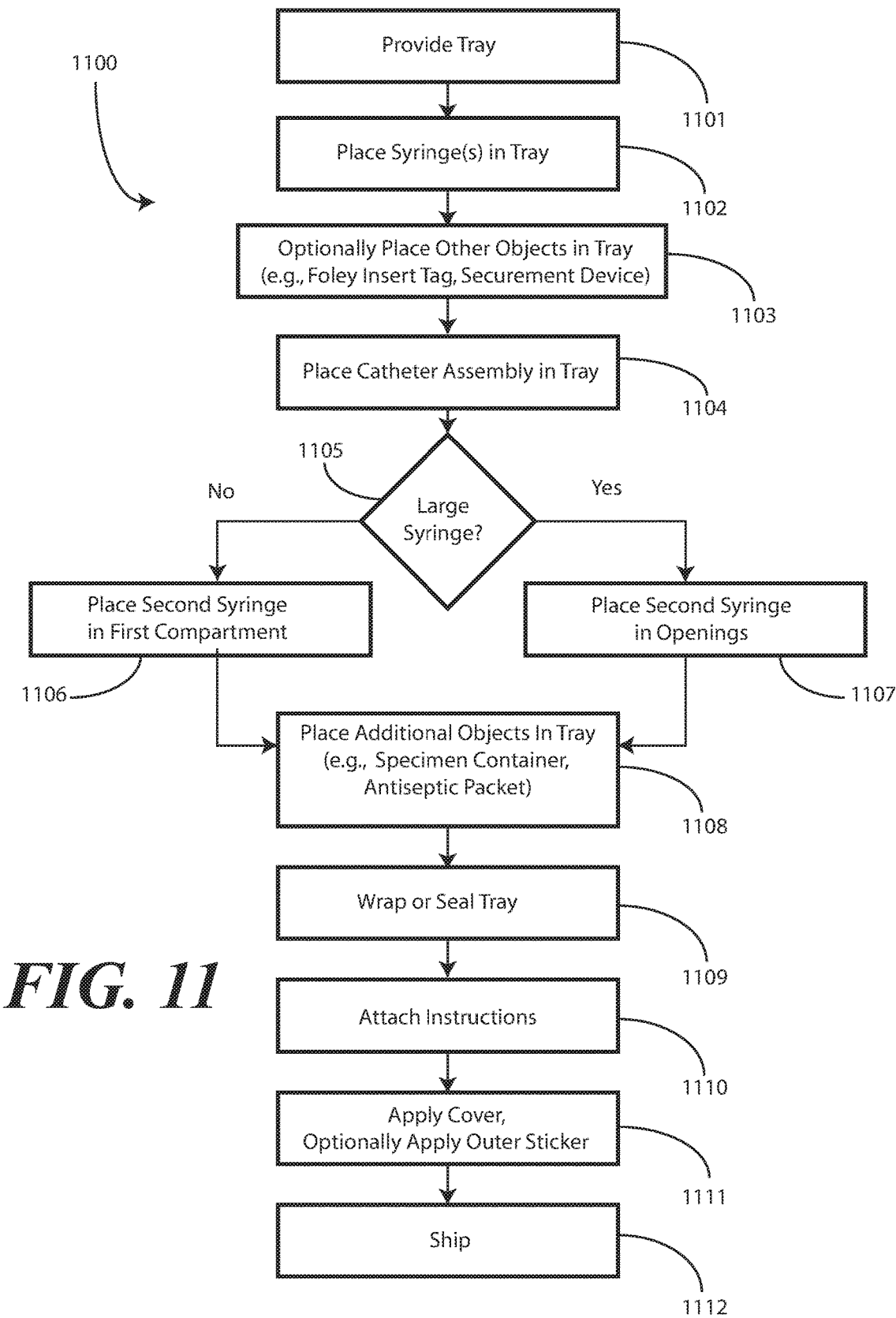
FIG. 11 illustrates a method of manufacturing one embodiment of a tray for a catheter or similar assembly, with a catheter and corresponding procedural devices disposed therein, in accordance with embodiments of the invention.

Turning now to FIG. 11, illustrated therein is a method 1100 for manufacturing a packaged catheter assembly in accordance with embodiments of the invention. At step 1101, the manufacturer provides a tray (100) having at least a first compartment (101) for accommodating one or more syringes (701,702) and a second compartment (102) for accommodating a flexible medical device, such as a catheter assembly (700). As noted above, in one embodiment the first compartment (101) will have a first compartment base member (107) having an inclined, stair-stepped contour (115). The first compartment (101) and second compartment (102) can be separated by a first barrier (105) having an opening (121) therein.

Once the tray (100) is procured, the manufacturer can dispose at least one syringe (701) in the first compartment (101) at step 1102. Optionally, at step 1103, the manufacturer may include additional components with the tray (100). For example, a catheter securement device, a Foley insert tag, or other complementary components may be included at this step 1103.

In one embodiment, as determined at decision 1105, a second syringe (702) will be disposed in the first compartment (101) at step 1106. In another embodiment, the second syringe (702) will be disposed laterally within the first opening (121) and, where present, a second opening (122) at step 1107.

At step 1104, the manufacturer will place the catheter assembly (700) in the second compartment (102). Other components may be disposed in the tray (100) as well, including a specimen container (703) that is disposed in a third compartment (103) at step 1108. Further, other devices may be included, such as towels, drapes, printed instructions, one or more antiseptic packets, and so forth. These other devices can be disposed in various compartments within the tray (100).

At step 1109, the tray (100) is sealed. This can be accomplished by folding a CSR wrap about the tray (100). In such an embodiment, the CSR wrap can be used during the catheter insertion procedure as well. At optional step 1110, the manufacturer can enclose printed instructions (1001). In one embodiment, the printed instructions (1001) will direct a user to discharge contents of at least one syringe into the first compartment (101) and to pass at least a portion of the catheter assembly (700) through the opening and into the contents to lubricate the catheter.

At step 1111, the manufacturer can place a sterile wrap about the tray (100) and the printed instructions (1001), where included. A sticker or other sealing device can be applied that indicates the contents to be sterile as well. At step 1112, the completed assembly can be shipped to a medical services provider.

Figure 12:
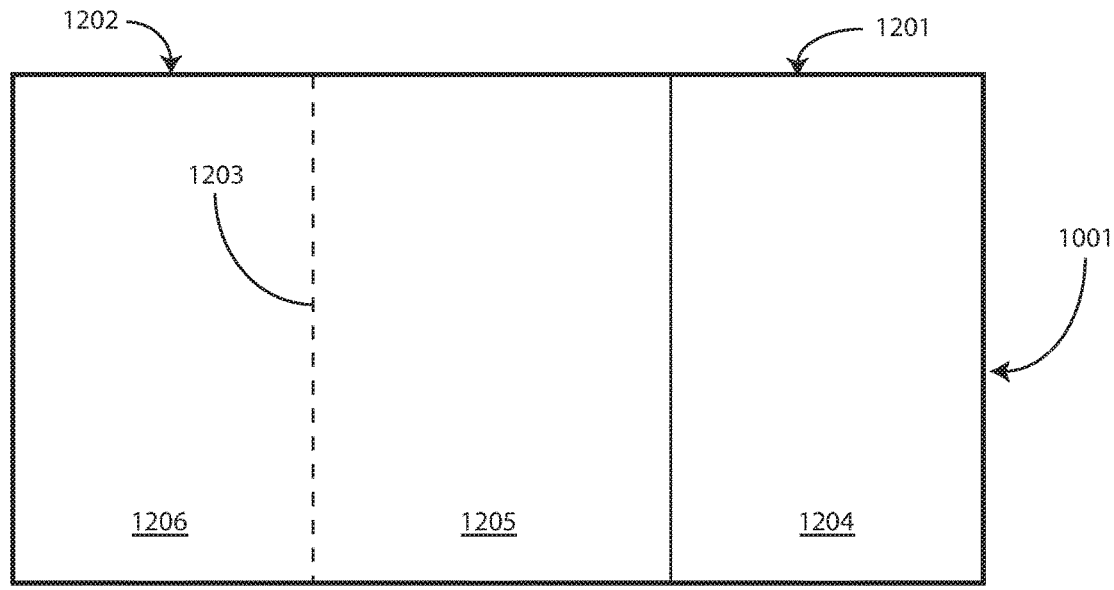
FIG. 12 illustrates one embodiment of printed instructions in accordance with embodiments of the invention.
Figure 13:
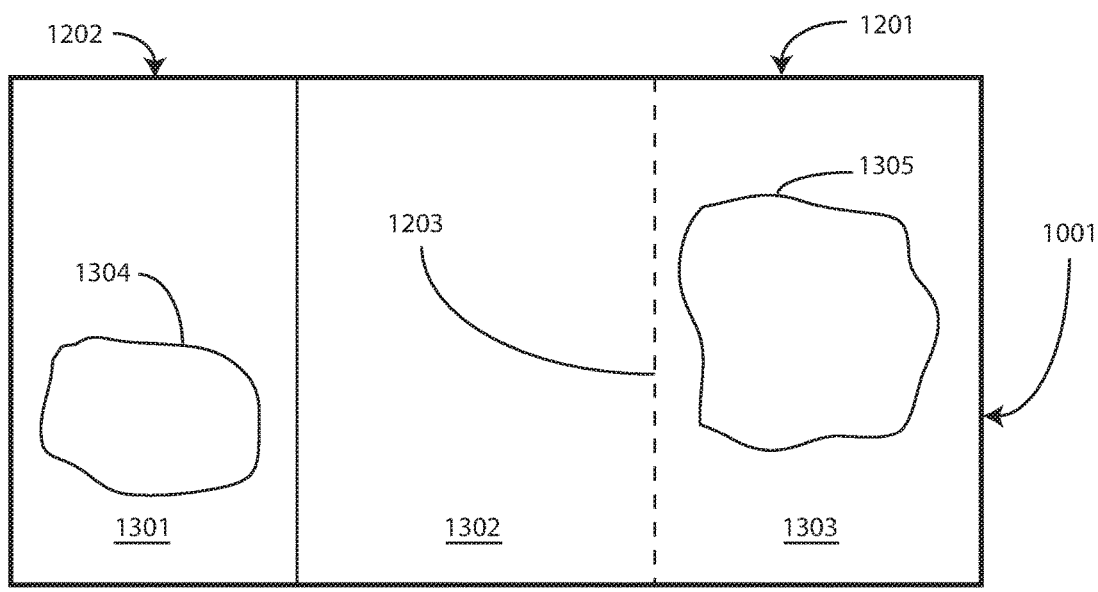
FIG. 13 illustrates one embodiment of printed instructions in accordance with embodiments of the invention.

Turning now to FIGS. 12-13, illustrated therein is one embodiment of the printed instructions 1001 in accordance with embodiments of the invention. The printed instructions 1001 can be configured as an instruction manual suitable for inclusion with a tray (100) as described above. FIG. 12 illustrates a view of a first side of the instruction manual, while FIG. 13 illustrates a view of a second side of the instruction manual.

In one embodiment, the printed instructions 1001 are configured as a two-portion instruction manual having a health care services portion 1201 and a patient portion 1202. In the illustrative embodiment of FIGS. 12-13, the patient portion 1202 is detachably coupled to the health care services portion 1201, and is thus separated from the health care services portion 1201, by a perforation 1203. For example, where the printed instructions 1001 are configured as a printed material on a paper-based stock, the perforation 1203 can be a perforated line running along a dimension of the printed instructions 1001 such that the printed instructions 1001 can be easily torn along the perforation 1203 to separate the patient portion 1202 from the health care services portion 1201.

In one embodiment, the printed instructions 1001 are configured as a plurality of panels 1204,1205,1206,1301, 1302,1303. As will be shown in FIG. 20, in one embodiment the printed instructions 1001 can be configured as an instruction manual that is formed with an accordion-style fold, with each of the panels 1204,1205,1206,1301,1302,1303 forming a page of the instruction manual. In the illustrative embodiment of FIGS. 12-13, panels 1204,1205 and panels 1301, 1302 form the health care services portion 1201, while panels 1206,1303 form the patient portion. Panels 1206, 1303 are separated from panels 1204,1205 and panels 1301, 1302 by the perforation 1203 such that the patient portion 1202 is tearably separable from the health care services portion 1201.

In one embodiment, the health care services portion 1201 includes instructions 1304 for using the catheter assembly and other corresponding medical devices disposed within the accompanying tray. The instructions 1304 can include text and/or figures or illustrations showing how to use the catheter assembly and corresponding medical devices on the patient, as well as instructions on preparation, taking samples, preventing infection, and so forth. The instructions 1304, in one embodiment, also include an instruction to detach the patient portion 1202, give the patient portion 1202 to the patient, as well as an instruction to discuss the information disposed on the patient portion 1202 with the patient.

Similarly, the patient portion 1202 may also include instructions 1305 and/or helpful suggestions for the patient who is undergoing the catheterization procedure. For instance, this information can include any one or more of the following: a description of what a catheter is, what the patient should know about the catheter, how to reduce the chance of getting an infection from the catheterization procedure, what infections commonly associated with catheterization procedures typically are, the symptoms associated with infections commonly associated with catheterization procedures, and information about using the catheter at home. Additionally, the patient portion 1202 may include custom information as well. For example, in one embodiment the patient portion 1202 includes an informational section configured such that the health care service provider's name and contact information can be written thereon. It will be clear to those of ordinary skill in the art having the benefit of this disclosure that the invention is not so limited. For example, additional types of health care service instructions or patient instructions or suggestions can also be included.

Turning now to FIGS. 14-19, illustrated therein are exemplary panels 1204,1205,1206,1301,1302,1303. These panels 1204,1205,1206,1301,1302,1303 are intended to illustrate exemplary instructions for the health care services portion (1201) and patient portion (1202) of an illustrative instruction manual for a catheter assembly and corresponding medical devices included with an accompanying tray (100). It will be clear that these panels 1204,1205,1206,1301,1302, 1303 and the information printed thereon can be varied in any number of ways without departing from the spirit and scope of the invention as described herein and recited in the following claims. For example, the number of panels can be varied. Additionally, the information printed thereon can be condensed, expanded, or altered without departing from the spirit and scope of the invention. Also, the exemplary information may be moved from the panels shown to other panels, as a particular application may warrant.

Figure 14:
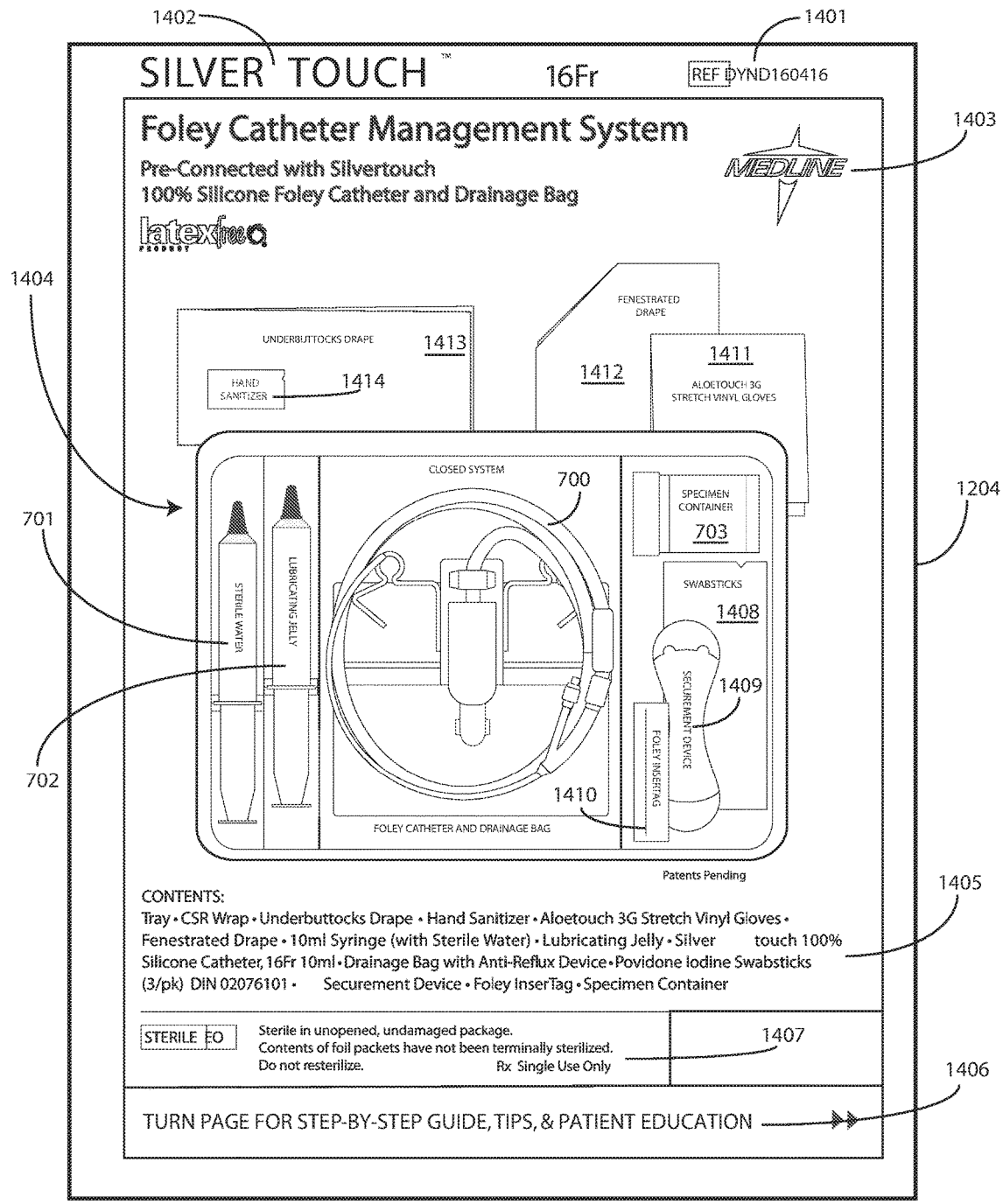

Beginning with FIG. 14, illustrated therein is one exemplary panel 1204. In one embodiment, panel 1204 will be configured such that when the catheter package assembly within which the instruction manual is disposed is initially opened, panel 1204 will be readily viewable. For example, where the catheter package assembly is assembled as shown in FIG. 10 above, once the sterile wrap (1002) is removed, the panel 1204 will be viewable prior to removal of the CSR wrap (1000).

Panel 1204 can include general information about the catheter assembly and corresponding medical devices disposed within the tray. For example, this information can include part number information 1401, trade name information 1402, and manufacturer information 1403. A diagram 1404 of the contents of the package assembly may be included as well. The illustrative diagram 1404 of FIG. 14 illustrates a tray 100 having a catheter assembly 700 and corresponding medical devices disposed therein. The corresponding medical devices of this illustrative embodiment include a pair of syringes 701,702 and a specimen container 703. Additionally swab sticks 1408, a catheter securement deice 1409, a Foley insert tag 1410, vinyl gloves 1411, a fenestrated drape 1411, an underbuttocks drape 1413, and a hand sanitizer 1414 solution or wipe are disposed within the tray 100.

In addition to a diagram 1404, panel 1204 can also include a written description 1407 of the elements included in the tray 100. Further, sterility information 1407 can be included. Panel 1204 can even include instructional material 1406 on how to use the instruction manual as well.

Figure 15:
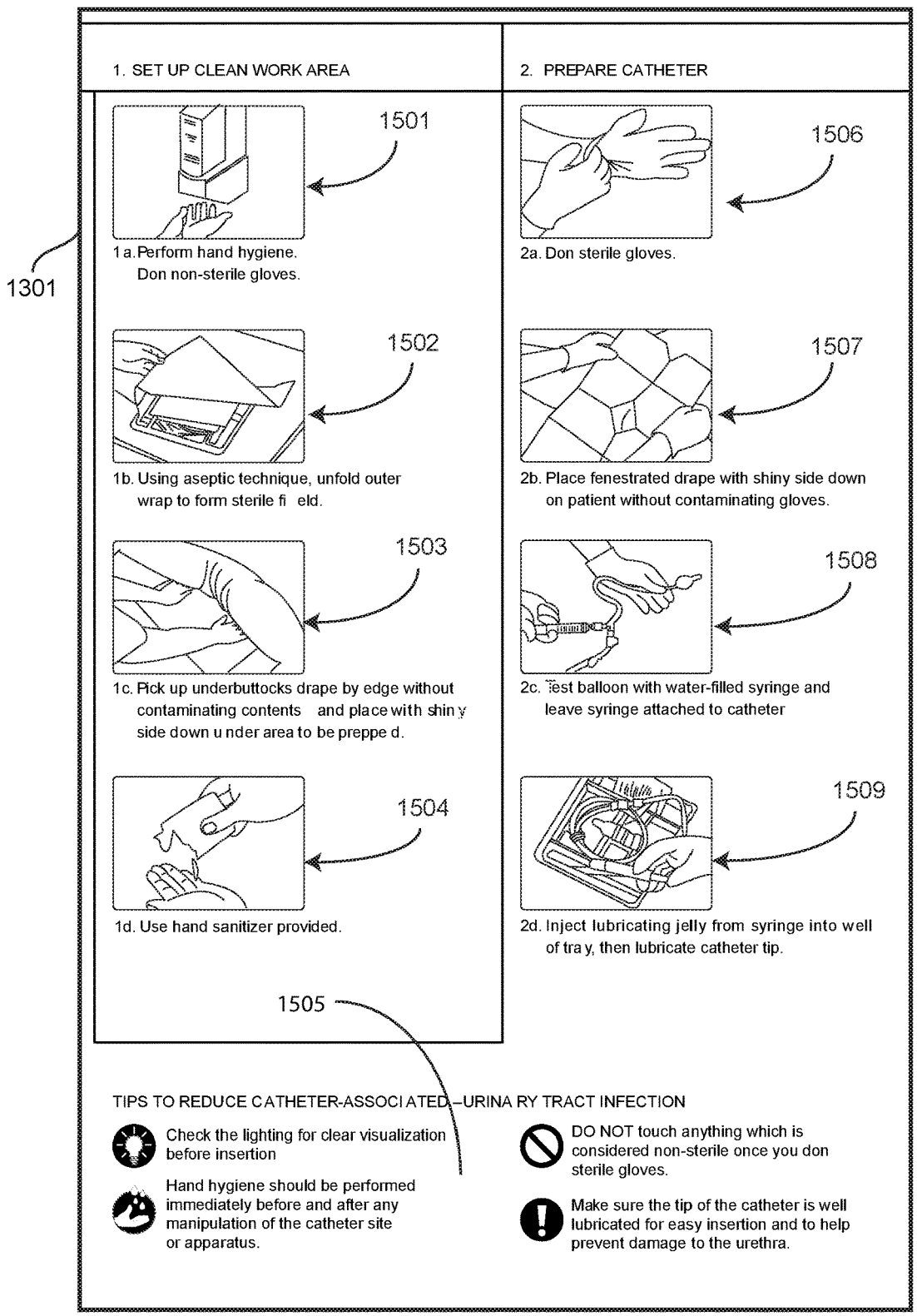

Turning now to FIG. 15, illustrated therein is one embodiment of panel 1301. As will be described below with respect to FIG. 20, in one embodiment the printed instructions (1001) are configured as an accordion-style folded instruction manual. In such a configuration, panel 1301 can be disposed on the back of panel 1204. Panel 1301 will therefore be visible upon a health care services provider opening the instruction manual.

Panel 1301 can include instructions for using the catheter assembly and the corresponding medical devices. As can be seen from this illustrative embodiment, panel 1301 can include instructions for setting up a clean work area. The instructions can include text, pictures, illustrations, or combinations of these.

In one embodiment, the instructions for setting up a clean work area include a hygiene performance step 1501, which may include instructions to wash hands, optionally put on gloves (which at this step can be non-sterile gloves), and so froth. The instructions may then include information on opening the remainder of the catheter package assembly. For instance, in FIG. 15 step 1502 indicates that the health care provider should remove the CSR wrap (1000), which in this case is folded about the tray (100). Note that in this illustrative embodiment, as the CSR wrap (1000) is folded about the tray (100), removal of the CSR wrap (1000) by unfolding creates a sterile field about the tray (100).

Step 1503 then instructs the health care provide to pick up the underbuttocks of the patient and to place the underbuttocks wrap beneath the patient. Step 1504 then instructs the health care provider to use the hand sanitizing solution provided with the catheter package assembly.

As with other panels shown in FIGS. 14-19, the various panels may include suggestions 1505 for preventing a catheter associated urinary tract infection. Some of this information is illustratively shown in FIG. 15. It will be understood that this information can be placed on one or more panels.

In addition to information for setting up a clean work area, in one embodiment panel 1301 includes instructions for preparing the catheter assembly (700) as well. For example, step 1506 instructs the health care services provider to don sterile gloves, as the hands were sanitized at step 1504. Step 1507 tells the health care services provider to place the fenestrated drape with a shiny side down on the patient without contaminating the sterile gloves donned at step 1506. Step 1508 instructs the health care services provider to test the balloon of the catheter assembly with the water-filled syringe stored in the first compartment. Step 1508 also instructs the health care services provider to leave the syringe connected to the catheter assembly.

Step 1509 then provides instructions on using the first compartment of the tray as a lubricant application chamber as described above. Specifically, in this illustrative embodiment, step 1509 instructs the health care services provider to inject the lubricating jelly found in the second syringe of the first compartment into the first compartment. Step 1509 also instructs the health care services provider to pass the tip of the catheter through the first opening in the wall separating the first compartment and second compartment into the lubricating jelly, thereby lubricating the tip of the catheter.

Figure 16:
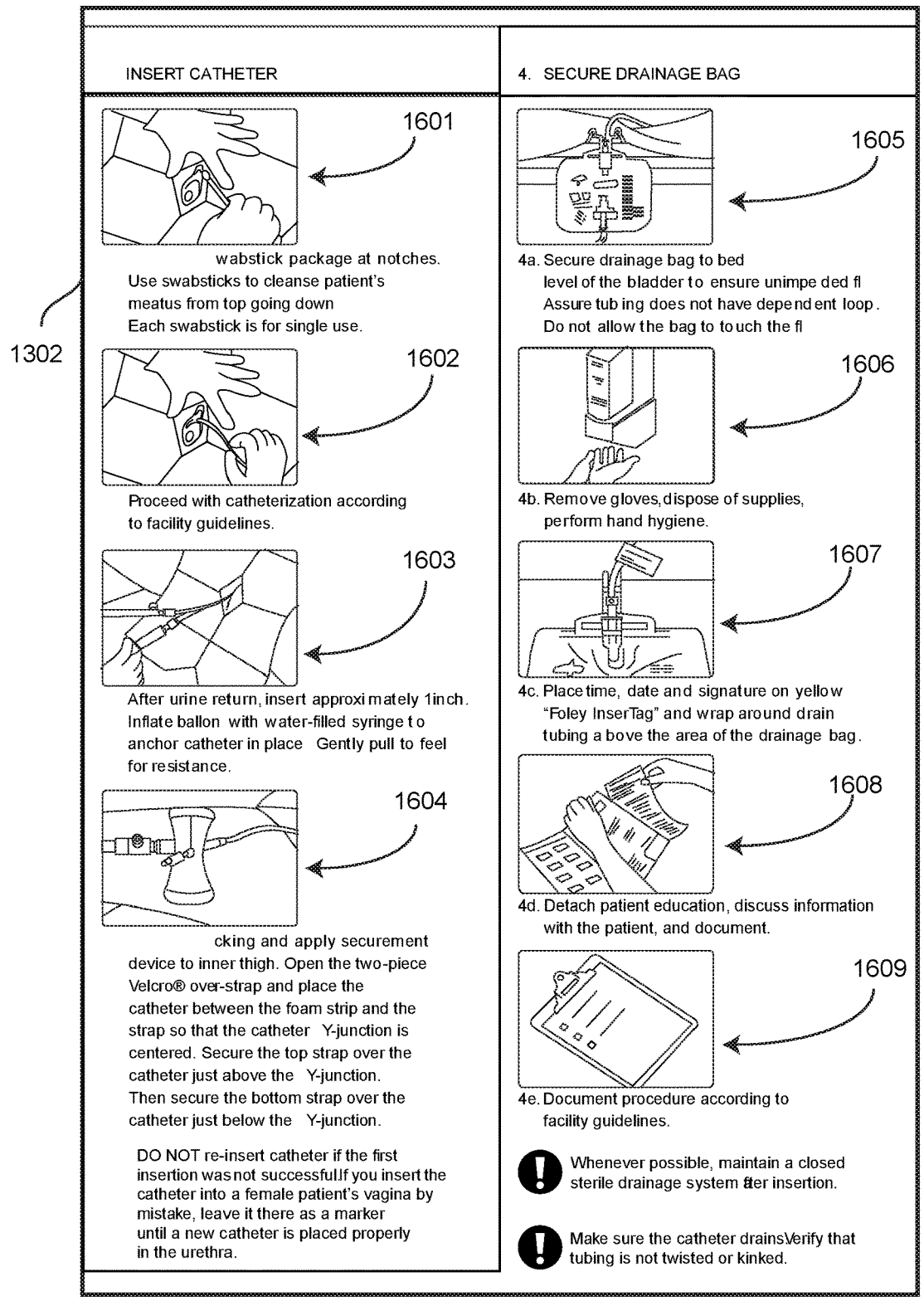

Turning now to FIG. 16, illustrated therein is an exemplary embodiment of panel 1302. The instructions printed thereon continue to provide the health care services provider with information regarding use of the catheter assembly. For example, in one embodiment, this information includes instructions on inserting the catheter.

At step 1601, the instructions direct the health care services provider to tear open the swab stick package and to use the swab sticks to clean the patient from the top down. The instruction also notes that each swab stick is intended for one use only to properly maintain the sterile field. Step 1602 directs the health care services provider to initiate the catheterization process by inserting the catheter assembly into the patient. Steps 1603 and 1604 continue this process as shown in FIG. 16.

Step 1605 directs the health care services provider to secure the drainage bag to the catheter assembly. Step 1606 directs the health care services provider to clean up upon completion of the catheterization process. Step 1607 provides instructions on completing the label on the Foley insertion tag included with the catheter package assembly and attaching it to the tubing or drain bag attached to the catheter assembly.

At step 1608, the health care services provider is instructed to detach the patient portion (1202) from the health care services portion (1201) by tearing the two apart along the perforation (1203). Step 1609 further instructs the health care services provider to discuss the patient information printed upon the patient portion (1202) with the patient. Step 1609 instructs that documentation of the entire procedure should be completed.

Figure 17:
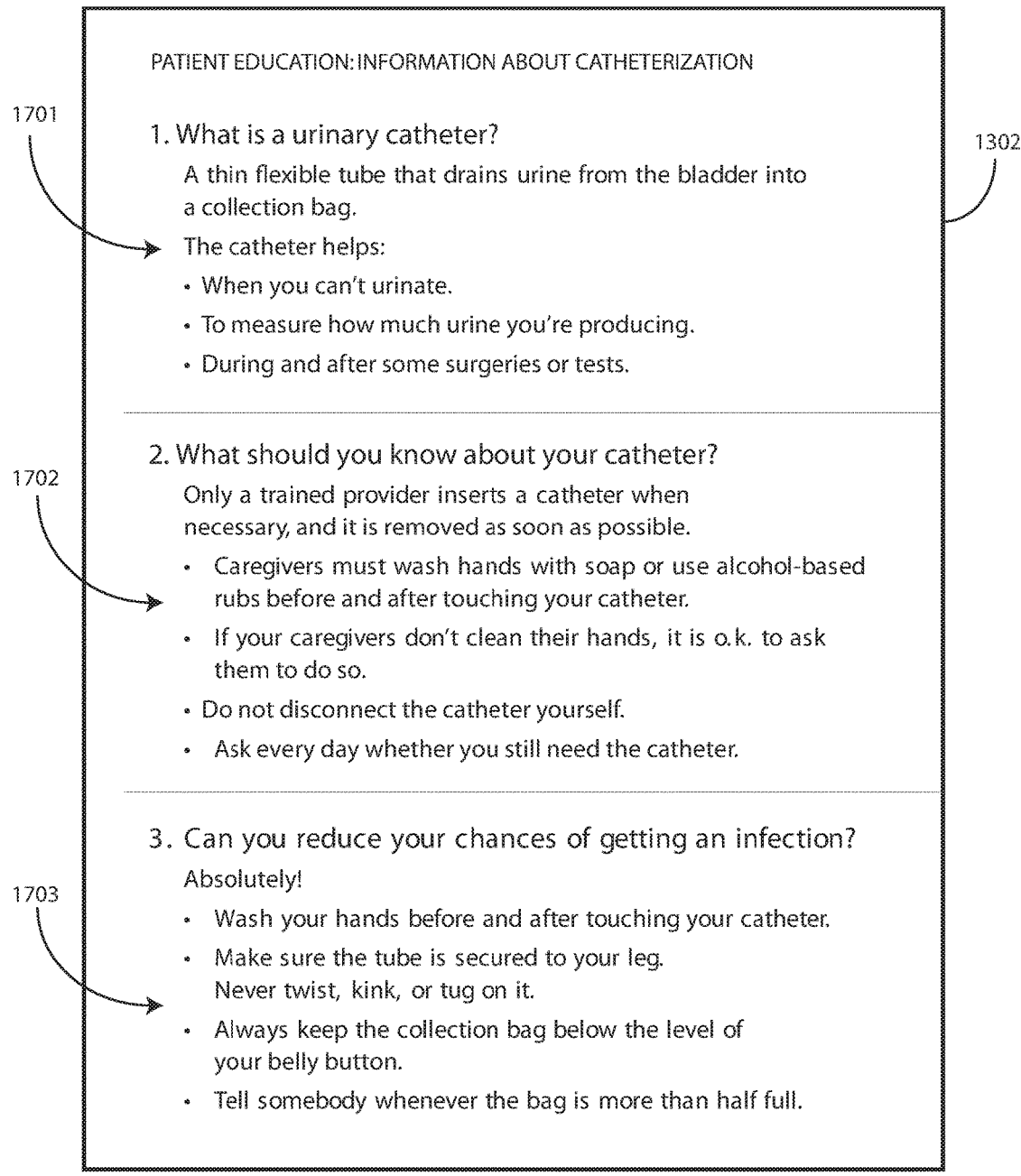

Turning now to FIG. 17, illustrate therein is one embodiment of panel 1303, which represents a first side of the patient portion (1202). This panel 1303 includes information 1701 describing what a catheter is and why a catheter might be used. The panel 1303 also includes information 1702 describing what the patient should know regarding catheters and catheter use. For example, this information 1702 might notify the patient that the health care services provider should wash hands prior to inserting the catheter, and that it is acceptable to ask them to do so if they have not done so before the patient.

The panel 1303 also includes information 1703 regarding how the patient can reduce the chances of getting an infection. This information 1703 can include a statement that the patient should wash their hands prior to touching the catheter assembly. The information 1703 may also include a statement that the drainage bag should always be kept at a level beneath the patient's navel, and that the patient should inform a helper when the bag is more than half full.

Turning to FIG. 18, illustrated therein is one embodiment of panel 1206. In this illustrative embodiment, panel 1206 forms the second side of the patient portion (1202) of the instruction manual, and accordingly, includes additional information that a patient may wish to know when using a catheter assembly.

By way of example, information 1801 informs the patient as to what common infections associated with catheter use are and how they are contracted. Information 1802 provides symptoms of these common infections, such as fever, blood in the urine, burning or painful urination, or frequent or more urgent urination after catheter removal. Information 1803 informs the patient of what they should know prior to going home after a catheter procedure.

Information 1804 comprises an informational section configured such that a health care provider's name and contact information may be written thereon. This is helpful to the patient in the event that the symptoms recited in information 1802 should arise after the procedure, in that the patient has readily available access to the information required to contact a physician or other health care provider. An advantage of having this information 1804 on the patient portion (1202) when the patient portion (1202) is detachable is that the patient can take it with them upon completion of the procedure.

Figure 19:
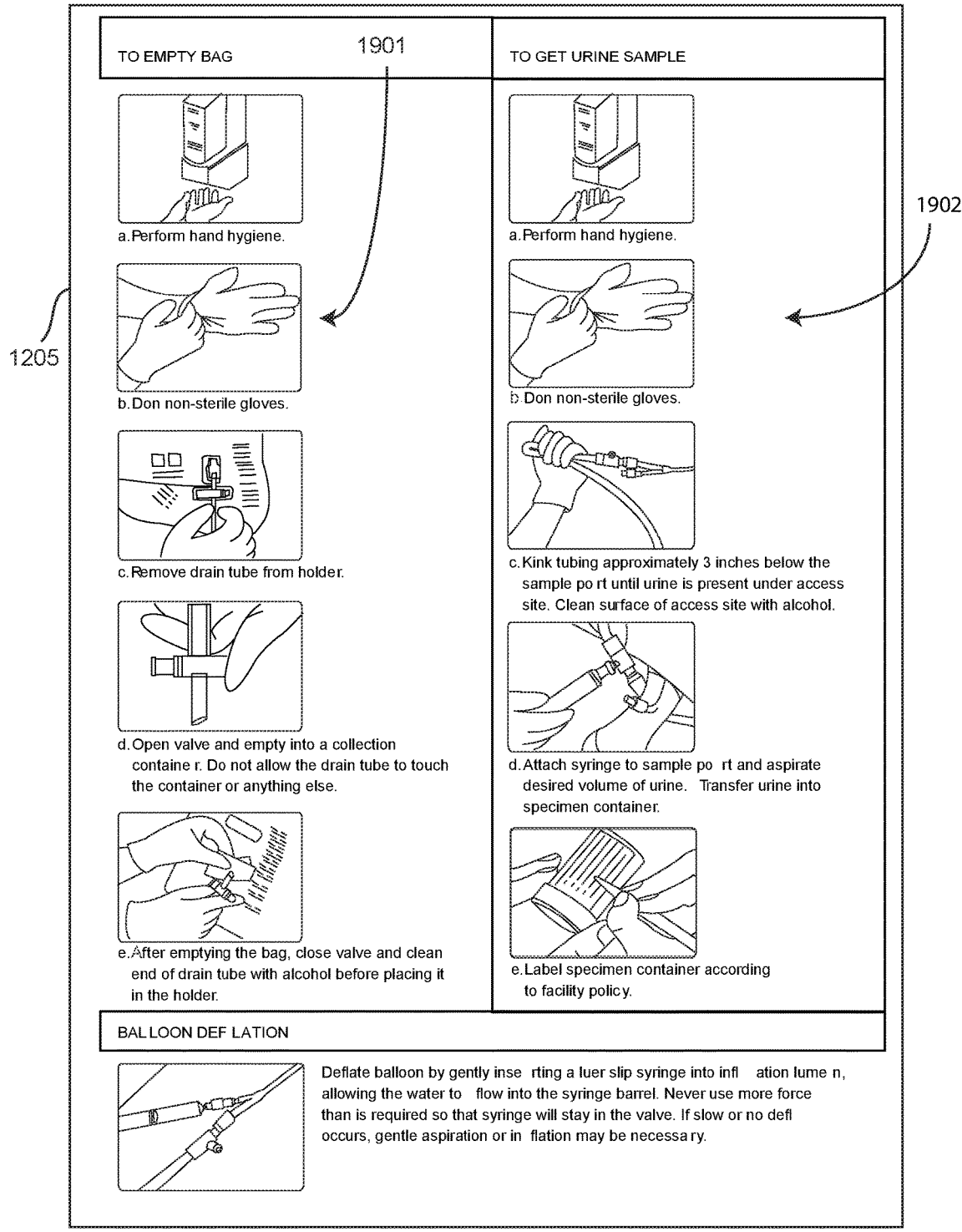

Turning now to FIG. 19, which is a portion of the health care services portion (1201), illustrated therein is one embodiment of panel 1205 that provides additional health services information. For example, information 1901 for emptying the drain bag and information 1902 describing how to obtain a urine sample can be included.

Figure 20:
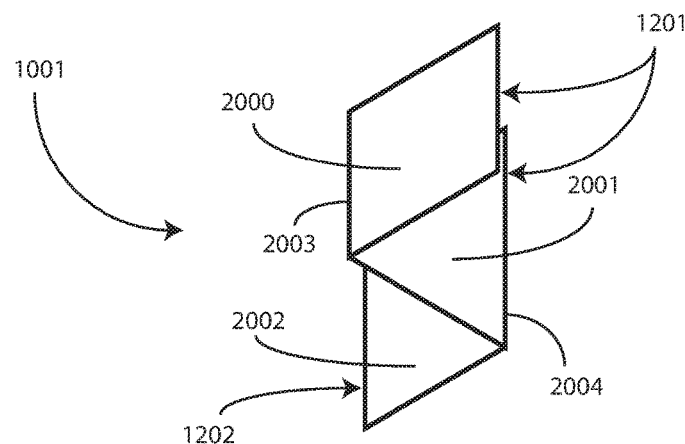
FIG. 20 illustrates a physical configuration of printed instructions in accordance with one embodiment of the invention.

Turning now to FIG. 20, illustrated therein is one physical configuration in which the printed instructions 1001 can be delivered along with the catheter package assembly in accordance with embodiments of the invention. FIG. 20 is but one of many configurations, and embodiments of the invention are not to be limited in this respect, as FIG. 20 is illustrative only.

In FIG. 20, the printed instructions 1001 are configures as a tri-section, accordion style bi-folded panel. Three sections 2000,2001,2002 are folded in an accordion style, with two folds 2003,2004 existing between the sections 2000,2001, 2002. When the printed instructions 1001 are configured as shown in FIGS. 12-13, folding the printed instructions 1001 in this manner allows the health care services portion 1201 to be disposed atop the patient portion 1202. Further, when the printed instructions are disposed atop a CSR wrap (1000) as shown in FIG. 10, by disposing the patient portion 1202 adjacent to the CSR wrap (1000), the health care services provider removing the sterile wrap (1002) off of the catheter package assembly will be assured of seeing the health care services portion 1201 first.

Figure 21:
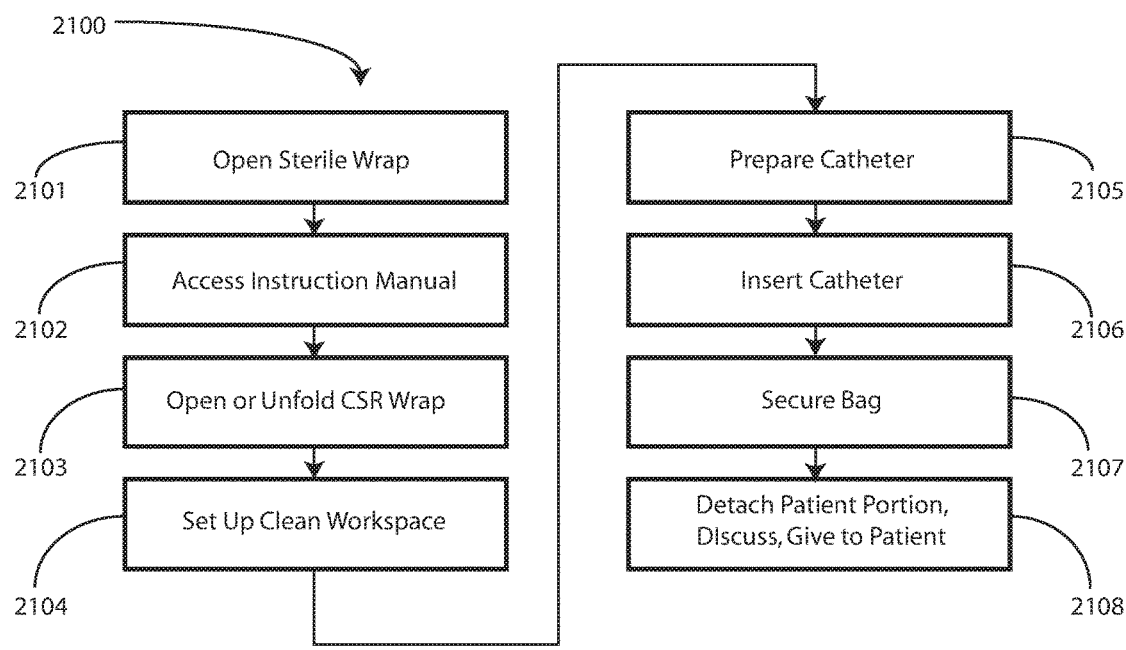
FIG. 21 illustrates a method in accordance with embodiments of the invention.

Turning now to FIG. 21, illustrated therein is a method 2100 of using the printed instructions (1001) as described herein. At step 2101, a health care services provider removes the sterile wrap (1002) disposed about the catheter package assembly. Where the catheter package assembly is configured as shown in FIG. 10, removal of the sterile wrap (1002) will reveal the printed instructions (1001). Where the printed instructions (1001) are configured as described in FIG. 20, with the patient portion (1202) disposed adjacent to the CSR wrap (1000), the health care services provider will see the health care services portion (1201) first.

At step 2102, the health care services provider accesses the printed instructions (1001) and begins to read the panels, which in one embodiment are panels configured in accordance with those described in FIGS. 14-19 above.

At step 2103, the health care services provider unfolds the outer CSR wrap (1000), which in one embodiment is then used to create a sterile field about the tray (100). At step 2104, the health care services provider prepares the workspace, which in one embodiment may be in accordance with steps (1501,1502,1503,1504) of panel (1301) in FIG. 15. For example, this may include donning non-sterile gloves, as shown at step (1501) of FIG. 15. This may further include picking up the underbuttocks drape, included with the tray (100), by the edge without contaminating the contents and placing the shiny side down under the area of the patient to be prepped as shown at step (1503) of FIG. 15. This may further include using the hand sanitizer as shown at step (1504 of FIG. 15.

At step 2105, the health care services provider prepares the catheter, which in one embodiment may be in accordance with steps (1506,1507,1508,1509) of panel (1301) as described in FIG. 15. For example, this can include donning sterile gloves as shown at step (1506) of FIG. 15. This may include placing a fenestrated drape, included with the tray (100), with the shiny side down on the patient without contaminating the sterile gloves, as shown at step (1507) of FIG. 15. This may include filling a test balloon of the catheter assembly with water as shown at step (1508) of FIG. 15, and injecting lubricating jelly from a syringe into the first compartment of the tray (100) as shown at step 1509 of FIG. 15.

At step 2106, the health care services provider inserts the catheter. In one embodiment, this can be in accordance with steps (1601,1602,1603,1604) of panel (1302) as described in FIG. 16. At step 2107, the health care provider secures the drain bag to the catheter assembly, which can be in accordance with steps (1605,1606,1607) described with respect to FIG. 16.

At step 2108, the health care services provider detaches the patient portion (1202) of the printed instructions (1001) from the health care services portion (1201). In one embodiment, this occurs by tearing the patient portion (1202) from the health care services portion (1201) along the perforation (1203), thereby transforming the printed instructions (1001) or instruction manual from a singular or unitary object into a two-piece object consisting of the patient portion (1202) and the health care services portion (1201). As described, above, the health care services provider may then discuss the patient portion (1202) with the patient and further give the patient portion (1202) to the patient to take home after the procedure.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A method of using a catheter package assembly, comprising:
   obtaining the catheter package assembly comprising:
      a single level tray having a Foley catheter coupled by a coiled tubing to a drainage bag disposed in a first compartment of the single level tray;
      one or more layers of wrap folded about the single level tray so as to enclose the single level tray within the one or more layers of wrap; and
      a sealed bag disposed about the single level tray and the one or more layers of wrap;
   unsealing the sealed bag disposed to access the one or more layers of wrap folded about the single level tray;
   creating a sterile field about the single level tray by unfolding the one or more layers of wrap, thereby revealing the single level tray;
   obtaining a first syringe from a second compartment of the single level tray; and
   forming a test balloon of the Foley catheter by injecting water from the first syringe into the Foley catheter.

2. The method of claim 1, further comprising:
   obtaining an underbuttocks wrap from the catheter package assembly; and
   placing the underbuttocks wrap beneath a patient.

3. The method of claim 2, further comprising obtaining a package of liquid hand sanitizer from the catheter package assembly and applying the package of liquid hand sanitizer.

4. The method of claim 3, further comprising obtaining a package of rubber gloves from the catheter package assembly and donning rubber gloves from the package of rubber gloves.

5. The method of claim 2, further comprising obtaining a fenestrated drape from the catheter package assembly and placing the fenestrated drape on the patient.

6. The method of claim 5, further comprising inserting the Foley catheter into the patient.

7. The method of claim 6, further comprising obtaining an instruction manual from the catheter package assembly, the instruction manual comprising:
   a health care services portion comprising instructions for using the Foley catheter and corresponding medical devices on the patient; and
   a patient portion, detachably coupled to the health care services portion and separated from the health care services portion by a perforation;
   detaching the patient portion; and
   delivering the patient portion to the patient.

8. The method of claim 7, further comprising writing a health care provider's name and contact information on the patient portion prior to the delivering the patient portion to the patient.

9. The method of claim 6, further comprising again inflating the test balloon in the Foley catheter by injecting the water from the first syringe into the Foley catheter to anchor the Foley catheter in the patient.

10. The method of claim 1, further comprising:
    obtaining a second syringe from the second compartment of the single level tray;
    injecting lubricating jelly from the second syringe into the second compartment of the single level tray; and
    passing at least a portion of the Foley catheter from the first compartment of the single level tray through an opening in a first barrier separating the second compartment from the first compartment prior to the inserting the Foley catheter into the patient.

11. The method of claim 10, further comprising:
    obtaining one or more swabsticks from a third compartment of the single level tray; and
    cleansing the patient with the one or more swabsticks prior to the inserting the Foley catheter into the patient.

12. The method of claim 1, further comprising obtaining a Foley insert tag from the single level tray.

13. The method of claim 12, further comprising attaching the Foley insert tag to one of the coiled tubing or the drainage bag.

14. The method of claim 13, further comprising emptying the drainage bag.

15. A method of using a catheter package assembly, comprising:
    unsealing a sealed bag disposed about a single level tray having a Foley catheter coupled by a coiled tubing to a drainage bag disposed therein;
    accessing an instruction manual comprising a health care services portion and a patient portion detachably coupled thereto;
    unfolding one or more layers of wrap to create a sterile field about the single level tray;
    removing at least one syringe from a first compartment in the single level tray;
    injecting lubricating jelly from the at least one syringe into the first compartment of the single level tray;
    obtaining the Foley catheter from a second compartment of the single level tray;
    passing at least a portion of the Foley catheter from the second compartment of the single level tray into the first compartment of the single level tray, thereby passing the at least the portion of the Foley catheter through the lubricating jelly;

inserting the at least the portion of the Foley catheter into a patient;

detaching the patient portion from the health care services portion; and delivering the patient portion to the patient.

16. The method of claim 15, further comprising:

obtaining an underbuttocks wrap from the catheter package assembly; and placing the underbuttocks wrap beneath the patient.

17. The method of claim 16, further comprising:

obtaining a package of liquid hand sanitizer from the catheter package assembly and applying the package of liquid hand sanitizer; and obtaining a package of rubber gloves from the catheter package assembly and donning rubber gloves from the package of rubber gloves;

wherein the obtaining the package of liquid hand sanitizer and the obtaining the package of rubber gloves occurs after the obtaining the underbuttocks wrap and the placing the underbuttocks wrap.

18. The method of claim 16, further comprising obtaining a fenestrated drape from the catheter package assembly and placing the fenestrated drape on the patient.

19. The method of claim 15, the passing the at least the portion of the Foley catheter from the second compartment of the single level tray into the first compartment of the single level tray further comprising:

passing the at least the portion of the Foley catheter through an opening in a first barrier separating the first compartment from the second compartment.

* * * * *